US012324854B2

(12) United States Patent
Rahmani Neishaboor

(10) Patent No.: US 12,324,854 B2
(45) Date of Patent: Jun. 10, 2025

(54) NANO-EMULSION BASED COMPOSITIONS, METHODS FOR THEIR PREPARATION AND THEIR USE IN DELIVERY OF ACTIVE INGREDIENTS

(71) Applicant: CANADIAN NANO PHARMACEUTICAL TECHNOLOGY INC., Richmond (CA)

(72) Inventor: Elham Rahmani Neishaboor, Richmond (CA)

(73) Assignee: CANADIAN NANO PHARMACEUTICAL TECHNOLOGY INC., Richmond (CA)

( * ) Notice: Subject to any disclaimer, the term of this patent is extended or adjusted under 35 U.S.C. 154(b) by 8 days.

(21) Appl. No.: 18/022,886

(22) PCT Filed: Aug. 26, 2020

(86) PCT No.: PCT/CA2020/051162
§ 371 (c)(1),
(2) Date: Feb. 23, 2023

(87) PCT Pub. No.: WO2022/040773
PCT Pub. Date: Mar. 3, 2022

(65) Prior Publication Data
US 2023/0225970 A1   Jul. 20, 2023

(51) Int. Cl.

| | |
|---|---|
| A01N 37/00 | (2006.01) |
| A01N 25/00 | (2006.01) |
| A01N 37/12 | (2006.01) |
| A01N 37/44 | (2006.01) |
| A61K 9/00 | (2006.01) |
| A61K 9/06 | (2006.01) |
| A61K 9/107 | (2006.01) |
| A61K 31/00 | (2006.01) |
| A61K 31/135 | (2006.01) |
| A61K 31/167 | (2006.01) |
| A61K 31/192 | (2006.01) |
| A61K 31/195 | (2006.01) |
| A61K 31/196 | (2006.01) |
| A61K 31/197 | (2006.01) |
| A61K 31/215 | (2006.01) |
| A61K 31/24 | (2006.01) |
| A61K 31/245 | (2006.01) |
| A61K 36/185 | (2006.01) |
| A61K 47/06 | (2006.01) |
| A61K 47/10 | (2017.01) |
| A61K 47/12 | (2006.01) |
| A61K 47/14 | (2017.01) |
| A61K 47/18 | (2017.01) |
| A61K 47/32 | (2006.01) |
| A61K 47/44 | (2017.01) |

(52) U.S. Cl.
CPC .......... *A61K 9/1075* (2013.01); *A61K 9/0014* (2013.01); *A61K 9/06* (2013.01); *A61K 31/135* (2013.01); *A61K 31/167* (2013.01); *A61K 31/192* (2013.01); *A61K 31/195* (2013.01); *A61K 31/196* (2013.01); *A61K 31/197* (2013.01); *A61K 31/245* (2013.01); *A61K 31/658* (2023.05); *A61K 36/185* (2013.01); *A61K 47/06* (2013.01); *A61K 47/10* (2013.01); *A61K 47/12* (2013.01); *A61K 47/14* (2013.01); *A61K 47/183* (2013.01); *A61K 47/32* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 5,985,177 | A | 11/1999 | Yoshida et al. |
| 9,220,784 | B2 | 12/2015 | Kisak et al. |
| 9,572,770 | B2 | 2/2017 | Queiroz |
| 2013/0085171 | A1 | 4/2013 | Ray, II et al. |

FOREIGN PATENT DOCUMENTS

| | | |
|---|---|---|
| CA | 2785249 | 6/2011 |
| CA | 2804591 | 1/2012 |
| CA | 2929910 | 5/2015 |
| CA | 3019208 | 10/2017 |
| CN | 109199879 | 11/2021 |
| WO | WO2020112595 | 6/2020 |

OTHER PUBLICATIONS

Nastiti et al., (2017) "Topical Nano and Microemulsions for Skin Delivery", Pharmaceutics, 9, 37, 25 pages.
Rahmani-Neishaboor et al., (2011) "Topical and Local Controlled Release of Stratifin for the Improvement of Hypertrophic Scarring in Open and Surgically Closed Wounds", Ph.D. Thesis, 137 pages.
Rahmani-Neishaboor et al., (2013) "Topical Application of a Film-Forming Emulgel Dressing that Controls the Release of Stratifin and Acetylsalicylic Acid and Improves/Prevents Hypertrophic Scarring", Wound Rep Reg 21, 55-65.
Shaker et al., (2019) "Nanoemulsion: A Review on Mechanisms for the Transdermal Delivery of Hydrophobic and Hydrophilic Drugs", Sci. Pharm. 87, 17, 34 pages.

*Primary Examiner* — Layla Soroush
(74) *Attorney, Agent, or Firm* — Rudy J. Ng; Bozicevic, Field & Francis LLP

(57) ABSTRACT

The present disclosure relates to compositions comprising an oil-in-water nano-emulsion dispersed in an external oil phase, methods for the preparation of such compositions as well as uses of such compositions, for example, for delivery of active ingredients to a subject. The methods comprise combining a first mixture comprising a liquid oil and a charged lipid with a second mixture that is an aqueous mixture comprising a film-forming thermoreversible emulsifier to prepare an oil-in-water nano-emulsion; and combining the oil-in-water nano-emulsion with a third mixture comprising a combination of solid lipids to prepare the composition.

23 Claims, 4 Drawing Sheets

NANO-EMULSION BASED COMPOSITIONS, METHODS FOR THEIR PREPARATION AND THEIR USE IN DELIVERY OF ACTIVE INGREDIENTS

FIELD

The present disclosure relates to compositions comprising an oil-in-water nano-emulsion dispersed in an external oil phase, methods for the preparation of such compositions as well as uses of such compositions, for example, for delivery of active ingredients to a subject.

BACKGROUND

Dermal and transdermal delivery of active ingredients such as drugs has the advantage of bypassing the hepatic first pass metabolism. It also can have the advantage of local targeted delivery of the active ingredient to the affected area. Accordingly, it may be more effective with less systemic side effects and drug-drug interactions than other routes of administration such as an oral delivery route. This may, for example, present a greater benefit in the management of chronic conditions such as chronic pain in elderly patients that may have high blood pressure and be using multiple medications resulting in increased drug-drug interactions.

Skin has three different layers i.e. epidermis, dermis and subcutaneous. The main barrier in transdermal delivery is the stratum corneum (SC), which is the outermost part among the five layers of epidermis. The composition of the SC and its morphology is unique in nature due to the tight junctions of corneocytes and with no blood vessels so that permeability of drugs through this layer of the skin is less. Due to this lower permeability, various prior formulations were not suitable for use as dermal and transdermal drug delivery systems.

Highly lipophilic drugs such as nonsteroidal anti-inflammatory drugs (NSAIDs) and cannabinoids have difficulty passing the stratum corneum. Therefore, if the transdermal delivery system is not appropriate, the desired analgesic and anti-inflammatory effect can only be achieved by increasing the concentration of active pharmaceutical ingredients (APIs) for example, to 30-40%. Incorporating a high concentration of APIs may, for example, require a higher concentration of solvent to levigate the dry powder prior to incorporating into the base. This significantly enhances the cost of a compounded drug for the patient and/or health care system and can also increase the risk of skin hypersensitivity reactions.

Acute and chronic inflammation and pain can be caused by many different reasons such as tissue or bone injury, nerve damage, arthritis and joint degeneration, prostaglandin-induced, neuropathic pain and/or musculoskeletal pain. Therefore, a personalized compounded product advantageously may contain various medications as well as optionally natural/herbal ingredients with a synergic effect to provide a tailored therapeutic outcome. As such, a delivery (e.g. transdermal) base for the management of e.g. inflammation and pain ideally has resilience to incorporate and deliver multiple actives without becoming unstable. These active ingredients may have hydrophilic and/or lipophilic physicochemical characteristics. Therefore, a useful compounding base for the treatment or management of inflammation and/or pain advantageously has the flexibility to enhance the delivery of both hydrophilic and lipophilic active ingredients.

Dermal and transdermal anti-inflammatory drugs for local pain relief are commercially available in the form of gels, creams, hydrogels and emulgels. Such topical NSAIDs in the form of gels, creams, hydrogels and emulgels provide 6 to 12 hours pain relief.

Pluronic lecithin organogels (PLOs) are the most popular conventional transdermal drug delivery systems in pharmacy compounding. PLOs have gained significant popularity compared to other traditional topical and transdermal drug delivery systems owing to their lower cost and high transdermal permeability. However, PLOs have a number of disadvantages such as a sticky tacky feeling, yellow color and short duration of action (e.g. 6-8 hours). As a result, patients may prefer a cosmetically appealing cream base rather than a gel base. Additionally, PLO gels can be difficult to mix with active ingredients at the pharmacy level due to a high concentration (20-30%) of a thermoreversible polymer, Poloxamer 407.

Conventional creams and liposomal delivery systems available in the market for the transdermal delivery of compounding APIs may have various drawbacks. For example, they may release the active ingredient fast and therefore require application frequently (for example, 3 to 4 times a day). They may also exhibit low rates and/or total amounts of penetration for certain active ingredients into the skin. Phase separation may occur if a high concentration of APIs such as cyclobenzaprine HCl, diclofenac Na, gabapentin, lidocaine HCl and/or ketamine HCl are added. They may also expire quickly when compounded with certain APIs (for example, 1 to 3 months). Currently available transdermal creams that provide 12-hour release and are robust can be expensive. Commercially available submicron transdermal emulgels made of Carbopol™ typically create a sticky and tacky feeling following application on skin. Additionally, these systems do not have the capacity to hold higher concentrations of APIs in salt form. Emulgels containing non-tacky colloidal gums such as xanthan, carrageenan, and tara gum may not provide sustained drug release.

A two-step emulsion technique has been conventionally used for creating oil-in-water-in-oil (O/W/O) multiple emulsions, in which an oil-in-water (O/W) type emulsion formed using a hydrophilic surfactant is re-emulsified in an outer oil phase in which a lipophilic surfactant has been dissolved. However, the emulsification stability of known multiple emulsions may be so low that, over time, phase separation occurs. Additionally, the inner oil phase can migrate into the outer oil phase thereby compromising the sustained release capacity. Therefore, creating an O/W/O emulsion that is, e.g. stable over a wide pH range and in the presence of a high load of electrolytes (e.g. an API in salt form) and also sustains the release of the API is desirable.

SUMMARY

As described in greater detail herein below, a nano-emulsion cream base (Nano-Emulsion SR Cream) was prepared that is a white cream that can, for example, be readily spread on an affected area without leaving a tacky or sticky feeling, readily removed if not tolerated, and would be readily mixed with compounding APIs at the pharmacy level. The Nano-Emulsion SR Cream is composed of an oil-in-water (O/W) nano-emulsion core stabilized in an external oil phase. Such oil-in-water-in-oil (O/W/O) multiple emulsions can be used, for example, to prolong the release of lipophilic and hydrophilic active ingredients. The Nano-Emulsion SR Cream possessed occlusive properties, which can enhance the percutaneous permeation of active ingredients but was still suitable for use on intact skin. The preservative challenge test showed that the formulation preserved against bacteria and mold growth. The Nano-Emulsion SR Cream was prepared using a low energy emulsification technique via hot stirring and homogenization. Such a technique can be an easy, cost-effective method to scale up. However, the choice of emulsion components and ratios of these components, as well as certain steps to add ingredients is critical in generating stable emulsion systems with appropriate particle sizes. The stability of a topical cream (e.g. a compounded product) plays an important role in the therapeutic efficacy of the formulation. The product was stable for 3 months under accelerated conditions, which corresponds to 2 years shelf life for the Nano-Emulsion SR cream. The Nano-Emulsion SR Cream was thermodynamically stable at least for 6 months even when diclofenac sodium was added at a 10% concentration. In addition, in vitro permeation release results showed that the Nano-Emulsion SR Cream sustained the release of diclofenac sodium for 24 hours. Such a cream can advantageously be applied once daily. This may, for example, result in enhanced patient adherence and compliance in comparison to formulations, which are only capable of release over a lower time such as 6-12 hours. It can also significantly reduce the cost of a drug for a patient with a chronic condition. When the Nano-Emulsion SR Cream was compounded with THC distillate and CBD oil, no oxidative discoloration of the cannabinoids was observed under the conditions used.

Accordingly, the present disclosure includes a composition comprising an oil-in-water nano-emulsion dispersed in an external oil phase, the oil-in-water nano-emulsion comprising an internal oil phase dispersed in an aqueous phase and stabilized by a film-forming thermoreversible emulsifier,
wherein
the internal oil phase comprises a liquid oil in combination with a charged lipid;
the external oil phase comprises a combination of solid lipids;
the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

In an embodiment, the aqueous phase further comprises a humectant. In another embodiment, the humectant is glycerin.

In an embodiment, the liquid oil is a synthetic oil, mineral oil, natural oil or combinations thereof. In another embodiment, the liquid oil is a vegetable oil or combination thereof. In a further embodiment, the liquid oil is medium-chain triglyceride (MCT) oil.

In an embodiment, the charged lipid is a negatively charged lipid. In another embodiment, the negatively charged lipid is oleic acid.

In an embodiment, the film-forming thermoreversible emulsifier is an amphoteric tri-block copolymer that is a polyethylene glycol-b-polypropylene glycol-b-polyethylene glycol (poloxamer). In another embodiment, the ratio by weight of the film-forming thermoreversible emulsifier to the internal oil phase is at least 0.1:10.

In an embodiment, the combination of solid lipids is a combination of at least two of
(i) glyceryl dibehenate, glyceryl palmitostearate or combinations thereof;
(ii) petrolatum, cetyl palmitate, beeswax or combinations thereof;
(iii) a hydrogenated vegetable oil or combinations thereof,
(iv) a fatty alcohol or combinations thereof, and
(v) glyceryl stearate, polyethylene glycol (PEG)-40 glyceryl stearate, PEG-100 stearate or combinations thereof.

In an embodiment, the cetyl palmitate, beeswax or combinations thereof is petrolatum. In another embodiment, the ratio by weight of (i):[(ii)+(iii)]:(v) in the combination of solid lipids is about 2:1:2. In a further embodiment, the solid lipids are glyceryl dibehenate, petrolatum, hydrogenated castor oil, cetyl alcohol, glyceryl stearate and PEG-100 stearate.

In an embodiment, the composition further comprises a multifunctional polymer, a liquid emollient, a penetration enhancer, a chelating agent, an antioxidant, a preservative or combinations thereof. In another embodiment, the composition comprises:
(i) a combination of multifunctional polymers that is polyacrylate crosspolymer-6 and hydroxyethyl acrylate/sodium acryloyldimethyl taurate copolymer;
(ii) the liquid emollient isopropyl lauroyl sarcosinate;
(iii) the penetration enhancer ethoxy diglycol;
(iv) the chelating agent disodium ethylenediaminetetraacetic acid (EDTA);
(v) the antioxidant butylated hydroxytoluene; and
(vi) a combination of preservatives that is caprylyl glycol and phenoxy ethanol.

In a further embodiment, the composition comprises, consists essentially of or consists of
water in an amount of from about 50 wt % to about 80 wt %;
glycerin in an amount of from about 1 wt % to about 10 wt %;
polyethylene glycol-b-polypropylene glycol-b-polyethylene glycol in an amount of from about 0.05 wt % to about 5 wt %;
oleic acid in an amount of from about 0.1 wt % to about 10 wt %;
MCT oil in an amount of from about 1 wt % to about 10 wt %;
polyacrylate crosspolymer-6 in an amount of from about 0.1 wt % to about 5 wt %;
hydroxyethyl acrylate/sodium acryloyldimethyl taurate copolymer in an amount of from about 0.1 wt % to about 5 wt %;
disodium EDTA in an amount of from about 0.005 wt % to about 0.05 wt %;
glyceryl dibehenate in an amount of from about 1 wt % to about 10 wt %;
petrolatum in an amount of from about 0.5 wt % to about 10 wt %;
hydrogenated castor oil in an amount of from about 1 wt % to about 10 wt %;
cetyl alcohol in an amount of from about 0.5 wt % to about 10 wt %;
glyceryl stearate and PEG-100 stearate in an amount of from about 1 wt % to about 10 wt %;
isopropyl lauroyl sarcosinate in an amount of from about 1 wt % to about 5 wt %;
ethoxy diglycol in an amount of from about 1 wt % to about 10 wt %;
butylated hydroxytoluene in an amount of from about 0.02 wt % to 0.1 wt %;
caprylyl glycol in an amount of from about 0.01 wt % to about 1.0 wt %; and phenoxy ethanol in an amount of from about 0.05 wt % to about 1 wt %.

In an embodiment, the oil droplets of the internal oil phase dispersed in the aqueous phase have a mean droplet size of less than about 700 nm.

In an embodiment, the composition is devoid of active ingredients. In another embodiment, such a composition has up to 2 years shelf life.

In an alternative embodiment, the composition further comprises one or more active ingredients. In another embodiment, such a composition releases the one or more active ingredients for a time of up to about 24 hours. In a further embodiment of the present disclosure, such a composition has at least 6 months shelf life.

In an embodiment, the active ingredient is diclofenac or a pharmaceutically acceptable salt thereof. In another embodiment, the diclofenac or pharmaceutically acceptable salt thereof is diclofenac sodium present in an amount of from about 5 wt % to about 10 wt %.

In an embodiment, the active ingredients are lidocaine, benzocaine, tetracaine or pharmaceutically acceptable salts thereof or combinations thereof, wherein the lidocaine, benzocaine, tetracaine or pharmaceutically acceptable salts thereof are present in an amount of up to about 20 wt %, with the total concentration of the lidocaine, benzocaine, tetracaine or pharmaceutically acceptable salts thereof being no more than 30 wt %, based on the total weight of the composition.

In an embodiment, the active ingredient is tetrahydrocannabinol (THC), cannabidiol (CBD) or combinations thereof. In another embodiment, the composition comprises CBD isolate in an amount of up to about 20 wt %, CBD oil in an amount of up to about 15 wt %, and/or THC distillate in an amount of up to 20 wt %.

In an embodiment, the composition further comprises one or more natural and/or herbal active agents with anti-inflammatory, analgesic or anesthetic effect; terpenoids; essential oils or combinations thereof.

The present disclosure also includes a use a composition of the present disclosure devoid of active ingredients for preparing a compound comprising one or more active ingredients.

The present disclosure also includes a use of a composition comprising one or more active ingredients of the present disclosure or a compound comprising one or more active ingredients of the present disclosure on the skin of a subject for delivering the one or more active ingredients to the subject. The present disclosure also includes a use of a compound comprising one or more active ingredients of the present disclosure or a compound comprising one or more active ingredients of the present disclosure for preparation of a medicament for the skin of a subject for delivering the one or more active ingredients to the subject. In an embodiment, such a composition or compound is for administration once per day. In another embodiment, the subject is a human.

The present disclosure also includes a method of preparing a composition comprising an oil-in-water nano-emulsion dispersed in an external oil phase, the oil-in-water nano-emulsion comprising an internal oil phase dispersed in an aqueous phase, the method comprising:
  combining a first mixture comprising a liquid oil and a charged lipid with a second mixture that is an aqueous mixture comprising a film-forming thermoreversible emulsifier to prepare an oil-in-water nano-emulsion; and
  combining the oil-in-water nano-emulsion with a third mixture comprising a combination of solid lipids to prepare the composition,
  wherein the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

In an embodiment, the aqueous mixture comprising the film-forming thermoreversible emulsifier further comprises a humectant. In another embodiment, the humectant is glycerin.

In an embodiment, the liquid oil is synthetic oil, mineral oil, natural oil or combinations thereof. In another embodiment, the liquid oil is a vegetable oil or combination thereof. In a further embodiment, the liquid oil is medium-chain triglyceride (MCT) oil.

In an embodiment, the charged lipid is a negatively charged lipid. In another embodiment, the negatively charged lipid is oleic acid.

In an embodiment, the film-forming thermoreversible emulsifier is an amphoteric tri-block copolymer that is a polyethylene glycol-b-polypropylene glycol-b-polyethylene glycol (poloxamer). In another embodiment, the ratio by weight of the film-forming thermoreversible emulsifier to the internal oil phase is at least 0.1:10.

In an embodiment, the combination of solid lipids is a combination of at least two of
  (i) glyceryl dibehenate, glyceryl palmitostearate or combinations thereof;
  (ii) petrolatum, cetyl palmitate, beeswax or combinations thereof;
  (iii) a hydrogenated vegetable oil or combinations thereof,
  (iv) a fatty alcohol or combinations thereof, and
  (v) glyceryl stearate, polyethylene glycol (PEG)-40 glyceryl stearate, PEG-100 stearate, or combinations thereof.

In an embodiment, the cetyl palmitate, beeswax or combinations thereof is petrolatum. In an embodiment, the ratio by weight of (i):[(ii)+(iii)]:(v) in the combination of solid lipids is about 2:1:2. In another embodiment, the solid lipids are glyceryl dibehenate, petrolatum, hydrogenated castor oil, cetyl alcohol, glyceryl stearate and PEG-100 stearate.

In an embodiment, the third mixture comprising the combination of solid lipids further comprises a liquid emollient, a penetration enhancer, an antioxidant, or combinations thereof. In another embodiment, the third mixture comprising the combination of solid lipids comprises: the liquid emollient isopropyl lauroyl sarcosinate; the penetration enhancer ethoxy diglycol; and the antioxidant butylated hydroxytoluene.

In an embodiment, subsequent to preparing the oil-in-water nano-emulsion, the method further comprises:
  combining the oil-in-water nano-emulsion with a fourth mixture comprising one or more of a multifunctional polymer and a chelating agent with the oil-in-water nano-emulsion.

In another embodiment of the present disclosure, the multifunctional polymer is a combination of multifunctional polymers that is polyacrylate crosspolymer-6 and hydroxyethyl acrylate/sodium acryloyldimethyl taurate copolymer and the chelating agent is disodium ethylenediaminetetraacetic acid (EDTA).

In an embodiment, subsequent to combining the oil-in-water nano-emulsion with the third mixture comprising a combination of solid lipids, the method further comprises combining the composition thereby obtained with a preservative. In another embodiment, the preservative is a combination of preservatives that is caprylyl glycol and phenoxy ethanol.

In an embodiment, the composition comprises, consists essentially of or consists of
- water in an amount of from about 50 wt % to about 80 wt %;
- glycerin in an amount of from about 1 wt % to about 10 wt %;
- polyethylene glycol-b-polypropylene glycol-b-polyethylene glycol in an amount of from about 0.05 wt % to about 5 wt %;
- oleic acid in an amount of from about 0.1 wt % to about 10 wt %;
- MCT oil in an amount of from about 1 wt % to about 10 wt %;
- polyacrylate crosspolymer-6 in an amount of from about 0.1 wt % to about 5 wt %;
- hydroxyethyl acrylate/sodium acryloyldimethyl taurate copolymer in an amount of from about 0.1 wt % to about 5 wt %;
- disodium EDTA in an amount of from about 0.005 wt % to about 0.05 wt %;
- glyceryl dibehenate in an amount of from about 1 wt % to about 10 wt %;
- petrolatum in an amount of from about 0.5 wt % to about 10 wt %;
- hydrogenated castor oil in an amount of from about 1 wt % to about 10 wt %;
- cetyl alcohol in an amount of from about 0.5 wt % to about 10 wt %;
- glyceryl stearate and PEG-100 stearate in an amount of from about 1 wt % to about 10 wt %;
- isopropyl lauroyl sarcosinate in an amount of from about 1 wt % to about 5 wt %;
- ethoxy diglycol in an amount of from about 1 wt % to about 10 wt %;
- butylated hydroxytoluene in an amount of from about 0.02 wt % to 0.1 wt %;
- caprylyl glycol in an amount of from about 0.01 wt % to about 1.0 wt %; and
- phenoxy ethanol in an amount of from about 0.05 wt % to about 1 wt %.

In an embodiment, the combining comprises mixing with a high shear homogenizer at a temperature of from about 35° C. to about 85° C.

In an embodiment, the method is for preparation of a compounding base.

In an alternative embodiment, the method further comprises adding one or more active ingredients, one or more natural and/or herbal active agents with anti-inflammatory, analgesic or anesthetic effect; terpenoids; essential oils or combinations thereof. In an embodiment, the addition is by a method comprising compounding. In an alternative embodiment, the addition is during the preparation of the composition.

The present disclosure also includes a composition obtained by a method of the present disclosure for preparing a composition comprising an oil-in-water nano-emulsion dispersed in an external oil phase, the oil-in-water nano-emulsion comprising an internal oil phase dispersed in an aqueous phase.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should rather be given the broadest interpretation consistent with the description as a whole.

BRIEF DESCRIPTION OF THE DRAWINGS

The embodiments of the disclosure will now be described in greater detail with reference to the attached drawings, in which.

DETAILED DESCRIPTION

I. Definitions

Figure 1:
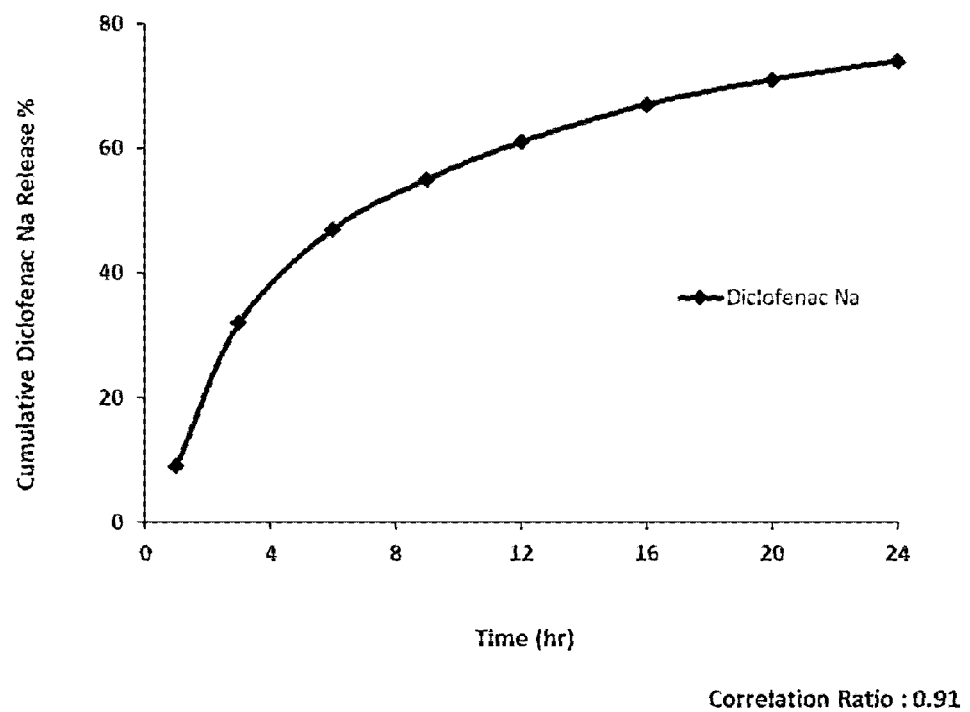
FIG. 1 is a plot showing cumulative diclofenac sodium (Diclofenac Na, percent) release as a function of time (hours) from a nano-emulsion SR composition according to an embodiment of the present disclosure tested by in vitro permeation through PermeaPad™ membranes.

Unless otherwise indicated, the definitions and embodiments described in this and other sections are intended to be applicable to all embodiments and aspects of the disclosure herein described for which they would be understood to be suitable by a person skilled in the art.

As used herein, the words "comprising" (and any form thereof, such as "comprise" and "comprises"), "having" (and any form thereof, such as "have" and "has"), "including" (and any form thereof, such as "include" and "includes") or "containing" (and any form thereof, such as "contain" and "contains"), are inclusive or open-ended and do not exclude additional, unrecited elements or process/method steps. As used herein, the word "consisting" and its derivatives are intended to be close-ended terms that specify the presence of the stated features, elements, components, groups, integers and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the term it modifies.

As used in this disclosure, the singular forms "a", "an" and "the" include plural references unless the content clearly dictates otherwise.

The term "and/or" as used herein means that the listed items are present, or used, individually or in combination. In effect, this term means that "at least one of" or "one or more" of the listed items is present or used.

The term "subject" as used herein includes all members of the animal kingdom including mammals. In an embodiment, the subject is a human.

The term "pharmaceutically acceptable salt" as used herein means a salt of the active ingredient that is compatible with the treatment of subjects and includes any suitable non-toxic organic or inorganic salt for the particular active ingredient.

II. Compositions

The compositions of the present disclosure are nano-emulsion based compositions that may be used topically for the sustained release cutaneous (dermal) and/or subcutaneous (transdermal) delivery of hydrophilic and lipophilic actives. For example, they can be used for the targeted local delivery of pharmaceuticals, cosmeceuticals, dermaceuticals, nutraceuticals, phytoceuticals and/or cannabinoids. The sustained drug release of the compositions together with enhanced permeation through skin may, for example, provide an advantageous cost saving benefit to patients and the health care system, by reducing the frequency and dose of application. Patient prescriptions may therefore last longer and the patient may require less frequent doctor and pharmacy visits.

Accordingly, the present disclosure includes a composition comprising an oil-in-water nano-emulsion dispersed in an external oil phase, the oil-in-water nano-emulsion comprising an internal oil phase dispersed in an aqueous phase and stabilized by a film-forming thermoreversible emulsifier,
  wherein
  the internal oil phase comprises a liquid oil in combination with a charged lipid;
  the external oil phase comprises a combination of solid lipids;
  the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

In an embodiment, the aqueous phase further comprises a humectant. The term "humectant" as used herein refers to a substance that can reduce and/or prevent the loss of moisture in the composition. The humectant can be any suitable humectant. In an embodiment, the humectant is glycerin, 1,2-propanediol, 1,3-propanediol or combinations thereof. In another embodiment, the humectant is glycerin. It will be appreciated by a person skilled in the art that glycerin is also sometimes referred to as glycerol. It will also be appreciated by a person skilled in the art that certain compounds such as glycerin, 1,2-propanediol and 1,3-propanediol are useful as and referred to herein as humectants, but they may also have other properties such as acting as a penetration enhancer and/or co-solvent. The compositions preferably have a low concentration of humectant, which advantageously may, for example, reduce transepidermal water loss (TEWL). Accordingly, in a further embodiment, the composition comprises less than about 2 wt % of the humectant (such as the glycerin).

The liquid oil is any suitable liquid oil or combination thereof. In an embodiment, the liquid oil is a synthetic oil, mineral oil, natural oil, essential oil or combinations thereof. In another embodiment, the liquid oil is synthetic oil, mineral oil, natural oil or combinations thereof. In a further embodiment, the liquid oil is a mineral oil, natural oil or combinations thereof. The term "synthetic oil" as used herein refers to a suitable cosmetic and/or pharmaceutical grade oil chemically synthesized from a plant, animal and/or mineral source or combinations of such synthetic oils. The term "mineral oil" as used herein refers to an oil made up of light mixtures of higher alkanes from a mineral source such as a distillate of petroleum. Mineral oils are typically colorless and odorless. The term "natural oil" as used herein refers to an oil obtained from a natural source, animal or plant. In an embodiment, the liquid oil is a natural oil. Natural oils can be obtained, for example, from oil-containing parts or combinations thereof of plants. Accordingly, in an embodiment, the natural oil is a vegetable oil or combination thereof. The term "vegetable oil" as used herein refers to an oil extracted from seeds and/or other oil-containing parts of a plant such as fruits. In another embodiment, the vegetable oil or combination thereof is selected from long chain triglycerides (i.e. triglycerides having an aliphatic tail of 13-21 carbon atoms), medium chain triglycerides (i.e. triglycerides having 2 or 3 fatty acids having an aliphatic tail of 6-12 carbon atoms), sources thereof or combinations thereof. A person skilled in the art would be able to readily select a suitable source or combination thereof for a particular composition of triglycerides. In an embodiment, the vegetable oil or combination thereof is selected from olive oil, avocado oil, moringa oil, medium chain triglyceride oil, coconut oil, palm oil and combinations thereof. In another embodiment, the liquid oil such as the vegetable oil or combination thereof is a medium-chain triglyceride (MCT) oil. In a further embodiment, the MCT oil comprises caprylic acid (C8:0) and capric acid (C10:0) e.g. in a ratio of about 60:40. The internal oil phase is in the range of from about 1 wt % to about 20 wt %, based on the total weight of the internal oil phase, aqueous phase and external oil phase. The term "essential oil" as used herein refers to a concentrated volatile composition of a plant-based oil.

The addition of oleic acid and vegetable oils with a high content of oleic acid in the nano-emulsions promoted a negative surface charge that increased electrostatic repulsive forces between droplets avoiding destabilization phenomena such as coalescence; i.e. the negatively charged oil droplets can enhance the nano-emulsion stability. Accordingly, in an embodiment, the charged lipid is a negatively charged lipid. In an embodiment, the negatively charged lipid is a negatively charged fatty acid. The negatively charged fatty acid can be any suitable negatively charged fatty acid. Negatively charged lipids e.g. fatty acids such as oleic acid may also, for example, advantageously cause less skin irritation than positively charged lipids such as fatty amines. Accordingly, in an embodiment, the negatively charged lipid is oleic acid. In another embodiment, the charged lipid is a positively charged lipid. In another embodiment, the positively charged lipid is a positively charged fatty amine. In another embodiment of the present disclosure, the positively charged fatty amine is oleyl amine.

In an embodiment, the ratio by weight of the liquid oil to the charged lipid is in a range of from about 5:1 to about 10:1.

Non-ionic emulsifiers such as sorbital esters and their ethoxylates, commercially available as Tween™ and Span, amphoteric emulsifiers such as phospholipids, lecithin, saponin and their derivatives have also been used to make nano-emulsions. However, in the compositions of the present disclosure, amphoteric tri-block copolymers are advantageously used, for example, because they can be used at lower concentration, such as a concentration as low as 0.2 wt % to create a stable nano-emulsion. Such tri-block copolymers are also preferred in chronic conditions such as but not limited to pain, inflammation and fibrosis as they may, for example, have less risk of skin irritation. The thermoreversible property (e.g. a liquid at room temperature and a gel at body temperature) of such emulsifiers may also be advantageous in sustaining the release of active ingredients. Accordingly, in an embodiment, the film-forming thermoreversible emulsifier is an amphoteric tri-block copolymer. Certain such film-forming thermoreversible emulsifiers that are amphoteric tri-block copolymers such as poloxamers (polyethylene glycol-b-polypropylene glycol-b-polyethylene glycol tri-block copolymers) can also enhance the viscosity of the water phase, thereby further enhancing the stability of a nano-emulsion. Accordingly, in an embodiment, the film-forming thermoreversible emulsifier is a polyethylene glycol-b-polypropylene glycol-b-polyethylene glycol. In another embodiment, the polyethylene glycol-b-polypropylene glycol-b-polyethylene glycol is Poloxamer 407 (Pluronic™ F-127), Poloxamer 188 (Pluronic™ F-68) or combinations thereof. In an embodiment, the polyethylene glycol-b-polypropylene glycol-b-polyethylene glycol is Poloxamer 407. The film-forming thermoreversible emulsifier is present in an amount suitable to stabilize the nano-emulsion. In an embodiment, the ratio by weight of the film-forming thermoreversible emulsifier to the internal oil phase is at least 0.1:10, e.g. at least 0.3:10.

The compositions of the present disclosure are sometimes referred to as oil-in-water-in-oil emulsions in that the oil-in-water nano-emulsion is further dispersed in the external oil phase. At least a portion of the solid lipids of the external oil phase are multifunctional in that they advantageously have more than one function in the composition; e.g. the capability to emulsify and stabilize the composition in addition to having thickening properties. For example, in some embodiments, the combination of solid lipids is a combination of at least two of: suitable mono-, di- and tri-glycerides or combinations thereof; a suitable occlusive wax or combinations thereof; a hydrogenated vegetable oil or combinations thereof; a fatty alcohol, fatty acid or combinations thereof; and suitable glyceryl esters, derivatives thereof and combinations thereof. Active pharmaceutical ingredients (APIs) in salt form such as cyclobenzaprine HCl, diclofenac sodium, ketamine HCl and lidocaine HCl are known to create a challenge with respect to the stability of cream dosage forms. For example, a high concentration of these APIs can cause breakdown of the cream due to their interaction with certain solid fats and thickening agents. In contrast, the compositions of the present examples were observed to be stable even with higher concentrations of diclofenac sodium.

In an embodiment, the combination of solid lipids is a combination of at least two of
(i) glyceryl dibehenate, glyceryl palmitostearate or combinations thereof;
(ii) petrolatum, cetyl palmitate, beeswax or combinations thereof;
(iii) a hydrogenated vegetable oil or combinations thereof,
(iv) a fatty alcohol, or combinations thereof, and
(v) glyceryl stearate, polyethylene glycol (PEG)-40 glyceryl stearate, PEG-100 stearate or combinations thereof.

For example, the glyceryl behenate and/or glyceryl palmitostearate have gelling and thickening properties, which may be advantageous for sustained release. In an embodiment, the glyceryl dibehenate, glyceryl palmitostearate or combinations thereof is glyceryl dibehenate. The petrolatum has thickening and semi-occlusive properties, may also enhance sustained release and compositions comprising petrolatum may have higher stability in the presence of an API in salt form than compositions comprising cetyl palmitate and/or beeswax. Accordingly, in an embodiment, the petrolatum, cetyl palmitate, beeswax or combinations thereof is petrolatum. In another embodiment, the petrolatum is petrolatum white USP. However, beeswax may be advantageous and/or desirable for certain compositions such as those comprising active ingredients that are cannabinoids. Accordingly, in another embodiment, the petrolatum, cetyl palmitate, beeswax or combinations thereof is beeswax. The hydrogenated vegetable oil or combination thereof can be useful to create a stable matrix. In an embodiment, the hydrogenated vegetable oil is hydrogenated castor oil, hydrogenated soy oil or combinations thereof. In another embodiment, the hydrogenated vegetable oil is hydrogenated castor oil. The petrolatum and/or hydrogenated vegetables oil(s) may also enhance the permeability of both hydrophilic and lipophilic drugs, for example, by hydrating the skin, dilating the SC intercellular channels and/or opening tight junctions. In an embodiment, the fatty alcohol or combination thereof is cetyl alcohol, stearyl alcohol, cetostearyl alcohol (a mixture of fatty alcohols comprising predominantly cetyl alcohol and stearyl alcohol) or combinations thereof. In another embodiment, the fatty alcohol is cetyl alcohol. The glyceryl stearate, polyethylene glycol (PEG)-40 glyceryl stearate, PEG-100 stearate or combinations thereof can be useful as viscosity enhancers and/or have self-emulsifying capability. In another embodiment, the glyceryl stearate, polyethylene glycol (PEG)-40 glyceryl stearate, PEG-100 stearate or combinations thereof is a combination of glyceryl stearate and PEG-100 stearate. In an embodiment, the ratio of the solid lipids (i):[(ii)+(iii)]:(v) in the combination is about 2:1:2. Such a ratio was observed to create a stable and sustained release matrix. In another embodiment, the solid lipids comprise, consist essentially of or consist of glyceryl dibehenate, petrolatum (e.g. petrolatum white USP), hydrogenated castor oil, cetyl alcohol, glyceryl stearate and PEG-100 stearate.

In another embodiment of the present disclosure, the composition further comprises a multifunctional polymer, a liquid emollient, a penetration enhancer, a chelating agent, an antioxidant, a preservative or combinations thereof. In an embodiment, the composition further comprises a multifunctional polymer. In another embodiment, the composition further comprises a liquid emollient. In another embodiment, the composition further comprises a penetration enhancer. In another embodiment, the composition further comprises an antioxidant. In another embodiment, the composition further comprises a preservative. In another embodiment, the composition further comprises a combination of a multifunctional polymer, a liquid emollient, a penetration enhancer, a chelating agent, an antioxidant and a preservative.

The "multifunctional polymer" as used herein refers to a polymer that has more than one function in the composition, for example, it has the capability to act as two or more of an emulsifier, a thickener, a stabilizer and a texturizer and includes a composition comprising a multifunctional polymer having such properties. In an embodiment, the multifunctional polymer comprises one or more tri-block copolymers having a hydrophilic-lipophilic balance (HLB) of about 18. In another embodiment, the multifunctional polymer is combination of polyacrylamide & C13-14 isoparaffin & laureth-7 (e.g. SEPIGEL™ 305), acrylamide/sodium acryloyldimethyl taurate copolymer, isohexadecane and Polysorbate 80 (e.g. SIMULGEL™ 600), a hydroxyethyl acrylate/sodium acryloyldimethyl taurate copolymer (e.g. SEPINOV™ WEO and/or SEPINOV EMT-10), polyacrylate crosspolymer-6 (e.g. SEPIMAX ZEN™), polyacrylate crosspolymer-11 (e.g. ARISTOFLEX™ Velvet) or combinations thereof. The multifunctional polymers are suitably selected from those that are stable in a wide pH range. For example, polyacrylate crosspolymer-6, has advantageous resistance to electrolytes and is stable in a wide pH range (from about 2 to about 8). It has the ability to stabilize the oil phase, provide a gel cream texture and create a pseudo-emulsion system. In an embodiment, the multifunctional polymer is a combination of multifunctional polymers that is polyacrylate crosspolymer-6 and hydroxyethyl acrylate/sodium acryloyldimethyl taurate copolymer.

The liquid emollient can be polar or non-polar and suitably has the ability to dissolve soluble and poorly water-soluble active ingredients, respectively. The liquid emollient is advantageously of amino acid or vegetable origin or is a silicone oil and has the advantage of a lack of a rancid oil odor. Accordingly, in an embodiment, the liquid emollient is isopropyl myristate, isopropyl palmitate, glycine, N-methyl-N-(1-oxododecyl)-, 1-methylethyl ester (isopropyl lauroyl sarcosinate), a plant-based C15-19 Alkane (e.g. EMOGREEN™) or a silicone oil emollient. Such emollients may, for example, have enhanced ceramide-like emolliency (sensory effect), reduced greasy feeling and/or reduced oxidative reactions (thereby avoiding or reducing the development of a rancid oil smell. In an embodiment of the present disclosure, the liquid emollient is isopropyl lauroyl sarcosinate.

Penetration enhancers suitably create a push and pull effect. As a result, they can enhance the skin reservoir effect and sustain the release of poorly soluble active ingredients. While dimethyl sulfoxide (DMSO) is a commonly used solvent for enhancing the penetration of lipophilic drugs, ethoxy diglycol is advantageous in that it has less skin toxicity. Accordingly, in an embodiment, the penetration enhancer is ethoxy diglycol. The Nano-Emulsion SR cream was also compatible and stable in the presence of terpenoids useful e.g. as natural penetration enhancers such as cineol, eucalyptol limonene, linanool and menthol. Accordingly, in some embodiments of the present disclosure, the penetration enhancer comprises a natural penetration enhancer. In another embodiment, the natural penetration enhancer is one or more terpenoids. In another embodiment, the terpenoid is cineol, eucalyptol limonene, linanool, menthol or combinations thereof. In another embodiment, the penetration enhancer comprises menthol.

The term "chelating agent" as used herein refers to a chemical compound that binds with metal ions or metallic compounds, thereby preventing or reducing oxidative reactions, enhancing the stability of product by improving preservative and/or antioxidant efficacy. The chelating agent is any suitable chelating agent. In an embodiment of the present disclosure, the chelating agent is a salt (e.g. a disodium salt) of ethylenediaminetetraacetic acid (EDTA).

Antioxidants can be useful, for example, to prevent or reduce oxidation of oil ingredients and/or discoloration of active ingredients such as cannabinoids. The antioxidants are suitably selected from natural or synthetic antioxidants. In an embodiment, the antioxidant is tocopherol acetate, butylated hydroxytoluene (BHT), butylated hydroxyanisole (BHA) or combinations thereof. In another embodiment, the antioxidant is butylated hydroxytoluene.

In some embodiments, the composition comprises a preservative that is a wide spectrum preservative or combination thereof capable of preserving both oil and water phases. The preservative is suitably selected from natural and/or synthetic preservatives. In an embodiment, the preservative is caprylyl glycol, pentylene glycol, ethylhexylglycerin, vitamin E, phenoxy ethanol or combinations thereof. In another embodiment of the present disclosure, the preservative is a combination of preservatives that is caprylyl glycol and phenoxy ethanol.

The present disclosure also includes a composition comprising an oil-in-water nano-emulsion dispersed in an external oil phase, the oil-in-water nano-emulsion comprising an internal oil phase dispersed in an aqueous phase and stabilized by a film-forming thermoreversible emulsifier,
wherein
the internal oil phase comprises a liquid oil in combination with a charged lipid;
the external oil phase comprises a combination of solid lipids;
the aqueous phase comprises a humectant;
the ratio by weight of the oil-in-water nano-emulsion to the external oil phase is in a range of from about 2:3 to about 7:3; and the ratio by weight of the liquid oil to the charged lipid is in a range of from about 5:1 to about 50:1,
the composition further comprising a multifunctional polymer, a liquid emollient, a penetration enhancer, a chelating agent, an antioxidant and a preservative.

In an embodiment, the composition comprises, consists essentially of or consists of
water (e.g. purified water);
the humectant glycerin;
the film-forming thermoreversible emulsifier that is a polyethylene glycol-b-polypropylene glycol-b-polyethylene glycol (e.g. Poloxamer 407);
the charged lipid oleic acid;
the liquid oil medium chain triglyceride (MCT) oil;
the combination of multifunctional polymers that is polyacrylate crosspolymer-6 and hydroxyethyl acrylate/sodium acryloyldimethyl taurate copolymer;
the chelating agent disodium ethylenediaminetetraacetic acid (EDTA);
the solid lipids glyceryl dibehenate, petrolatum (e.g. petrolatum white USP), hydrogenated castor oil, cetyl alcohol, glyceryl stearate and PEG-100 stearate;
the liquid emollient isopropyl lauroyl sarcosinate;
the penetration enhancer ethoxy diglycol;
the antioxidant butylated hydroxytoluene; and
the combination of preservatives that is caprylyl glycol and phenoxy ethanol.

In an embodiment, the water is present in an amount of from about 50 wt % to about 80 wt %, about 60 wt % to about 70 wt % or about 62 wt %. In another embodiment, the humectant (e.g. glycerin) is present in an amount of from about 1 wt % to about 10 wt %, about 1.5 wt % to about 5 wt % or about 2 wt %. In another embodiment, the film-forming thermoreversible emulsifier (e.g. the polyethylene glycol-b-polypropylene glycol-b-polyethylene glycol such as Poloxamer 407 is present in an amount of from about 0.05 wt % to about 5 wt %, about 0.1 wt % to about 0.5 wt % or about 0.3 wt %. In another embodiment, the charged lipid (e.g. the negatively charged lipid such as oleic acid) is present in an amount of from about 0.1 wt % to about 10 wt %, about 0.5 wt % to about 2.5 wt % or about 1 wt %. In another embodiment, the liquid oil (e.g. medium chain triglyceride (MCT) oil) is present in an amount of from about 1 wt % to about 10 wt %, about 7 wt % to about 9 wt % or about 8 wt %. In another embodiment, the multifunctional polymer (e.g. the combination of multifunctional polymers that is polyacrylate crosspolymer-6 and hydroxyethyl acrylate/sodium acryloyldimethyl taurate copolymer) is present in a total amount of from about 0.2 wt % to about 10 wt %, about 0.4 wt % to about 1.2 wt % or about 0.8 wt %. In some embodiments wherein the multifunctional polymer is a combination of polyacrylate crosspolymer-6 and hydroxyethyl acrylate/sodium acryloyldimethyl taurate copolymer, the polyacrylate crosspolymer-6 is present in an amount of from about 0.1 wt % to about 5 wt %, about 0.2 wt % to about 1 wt % or about 0.6 wt % and the hydroxyethyl acrylate/sodium acryloyldimethyl taurate copolymer is present in an amount of from about 0.1 wt % to about 5 wt %, about 0.1 wt % to about 1 wt % or about 0.2 wt %. In another embodiment, the chelating agent (e.g. disodium ethylenediaminetetraacetic acid) is present in an amount of from about 0.005 wt % to about 0.05 wt %, about 0.01 wt % to about 0.03 wt % or about 0.02 wt %. In another embodiment, the solid lipids are present in a total amount of from about 5 wt % to about 40 wt %. In some embodiments, solid lipid (i) (e.g. glyceryl dibehenate) is present in an amount of from about 1 wt % to about 10 wt %, about 5 wt % to about 6 wt % or about 5.5 wt %; solid lipid (ii) (e.g. petrolatum such as petrolatum white USP) is present in an amount of from about 0.5 wt % to about 10 wt %, about 0.75 wt % to about 1.25 wt % or about 1 wt %; solid lipid (iii) (e.g. hydrogenated castor oil) is present in an amount of from about 1 wt % to about 10 wt %, about 1.25 wt % to about 2.25 wt % or about 1.75 wt %; solid lipid (iv) (e.g. cetyl alcohol) is present in an amount of from about 0.5 wt % to about 10 wt %, about 0.75 wt % to about 5 wt % or about 2 wt %; and solid lipid (v) (e.g. glyceryl stearate and PEG-100 stearate) is present in an amount of from about 1 wt % to about 10 wt %, about 5 wt % to about 6 wt % or about 5.5 wt %. In another embodiment, the liquid emollient (e.g. isopropyl lauroyl sarcosinate) is present in an amount of from about 1 wt % to about 5 wt %, about 2 wt % to about 4 wt % or about 3 wt %. In another embodiment, the penetration enhancer (e.g. ethoxy diglycol) is present in an amount of from about 1 wt % to about 10 wt %, about 4 wt % to about 6 wt % or about 5 wt %. In another embodiment, the antioxidant butylated hydroxytoluene is present in an amount of from about 0.02 wt % to about 0.1 wt %, about 0.05 wt % to less than 0.1 wt % or less than 0.1 wt %. In another embodiment, the preservative (e.g. the combination of preservatives that is caprylyl glycol and phenoxy ethanol) is present in a total amount of from about 0.06 wt % to about 2.0 wt %. In some embodiments wherein the preservative is a combination of preservatives that is caprylyl glycol and phenoxy ethanol, the caprylyl glycol is present in an amount of from about 0.01 wt % to about 1.0 wt %, about 0.4 wt % to about 0.6 wt % or about 0.5 wt % and the phenoxy ethanol is present in an amount of from about 0.05 wt % to about 1 wt %, about 0.85 wt % to about 0.95 wt % or about 0.9 wt %. It will be appreciated by a person skilled in the art that the ranges in such embodiments can be optionally be interchanged.

In an embodiment, the composition comprises, consists essentially of or consists of water in an amount of from about 50 wt % to about 80 wt %, about 60 wt % to about 70 wt % or about 62 wt %; glycerin in an amount of from about 1 wt % to about 10 wt %, about 1.5 wt % to about 5 wt % or about 2 wt %; polyethylene glycol-b-polypropylene glycol-b-polyethylene glycol (e.g. Poloxamer 407) in an amount of from about 0.05 wt % to about 5 wt %, about 0.1 wt % to about 0.5 wt % or about 0.3 wt %; oleic acid in an amount of from about 0.1 wt % to about 10 wt %, about 0.5 wt % to about 2.5 wt % or about 1 wt %; medium chain triglyceride (MCT) oil in an amount of from about 1 wt % to about 10 wt %, about 7 wt % to about 9 wt % or about 8 wt %; polyacrylate crosspolymer-6 in an amount of from about 0.1 wt % to about 5 wt %, about 0.2 wt % to about 1 wt % or about 0.6 wt %; hydroxyethyl acrylate/sodium acryloyldimethyl taurate copolymer in an amount of from about 0.1 wt % to about 5 wt %, about 0.1 wt % to about 1 wt % or about 0.2 wt %; disodium ethylenediaminetetraacetic acid in an amount of from about 0.005 wt % to about 0.05 wt %, about 0.01 wt % to about 0.03 wt % or about 0.02 wt %; glyceryl dibehenate in an amount of from about 1 wt % to about 10 wt %, about 5 wt % to about 6 wt % or about 5.5 wt %; petrolatum (e.g. petrolatum white USP) in an amount of from about 0.5 wt % to about 10 wt %, about 0.75 wt % to about 1.25 wt % or about 1 wt %; hydrogenated castor oil in an amount of from about 1 wt % to about 10 wt %, about 1.25 wt % to about 2.25 wt % or about 1.75 wt %; cetyl alcohol in an amount of from about 0.5 wt % to about 10 wt %, about 0.75 wt % to about 5 wt % or about 2 wt %; glyceryl stearate and PEG-100 stearate in an amount of from about 1 wt % to about 10 wt %, about 5 wt % to about 6 wt % or about 5.5 wt %; isopropyl lauroyl sarcosinate in an amount of from about 1 wt % to about 5 wt %, about 2 wt % to about 4 wt % or about 3 wt %; ethoxy diglycol in an amount of from about 1 wt % to about 10 wt %, about 4 wt % to about 6 wt % or about 5 wt %; butylated hydroxytoluene in an amount of from about 0.02 wt % to 0.1 wt %, about 0.05 wt % to less than 0.1 wt % or less than 0.1 wt %; caprylyl glycol in an amount of from about 0.01 wt % to about 1.0 wt %, about 0.4 wt % to about 0.6 wt % or about 0.5 wt %; and phenoxy ethanol in an amount of from about 0.05 wt % to about 1 wt %, about 0.85 wt % to about 0.95 wt % or about 0.9 wt %.

The term "oil-in-water nano-emulsion" as used herein refers to an emulsion in which oil droplets of the internal oil phase dispersed in the aqueous phase have a mean droplet size of less than about 1 m. In an embodiment, the oil droplets have a mean droplet size of less than about 700 nm. In another embodiment, the oil droplets have a mean droplet size of less than about 500 nm. In a further embodiment, the oil droplets have a mean droplet size of from about 400 nm to about 600 nm or about 500 nm. Droplet size is suitably measured at ambient temperature (e.g. at 25° C.) using an instrument such as a Malvern Zetasizer Nano-ZS.

The pH of the composition may depend, for example, on whether the composition is in the form of a compounding base or in a form that would be directly applied to the skin of a subject and the skilled person would be able to select a suitable pH accordingly. For example, the pH of a composition that is in the form of a compounding base for use with an active ingredient that is of basic pH is suitably in a range that, when the active ingredient is added, the pH of the final composition is in a range that would be compatible with the application to the skin of a subject. This may, for example, be an operational advantage for compounding pharmacies with limited access to measuring pH devices. Alternatively, in some embodiments, a pH adjusting agent is added such that the pH of the final composition is in a range that would be compatible with the application to the skin of a subject. As a general rule, the compatible pH range for a composition to be applied to the skin of a subject is in a range of from greater than 4 to less than 8. Accordingly, as an example, a composition that is for compounding with about 10% diclofenac Na would optionally have a pH in a range of about 4.5 to about 5.5 which can prepare a final composition having a pH in a range of about 6.5 to less than 8 without the need to adjust the pH.

The compositions of the present disclosure may permit the topical administration of a single active ingredient or multiple active ingredients simultaneously to address one or more disease conditions. For example, the composition may sustain the release of both lipophilic and hydrophilic active ingredients, enhance the dermal and/or transdermal penetration of both lipophilic and hydrophilic active ingredients, exhibit resiliency in the presence of a salt load of up to 20% of the total weight of the composition or greater, and/or remain stable and/or avoid degradation for up to six months or more. The compositions of the present disclosure may provide for about 70% or greater permeation of a highly lipophilic active ingredient, such as diclofenac sodium (diclofenac Na), beyond the stratum corneum for up to about 24 hours.

Accordingly, in some embodiments, the composition delivers one or more active ingredients dermally (cutaneously) and/or transdermally (subcutaneously). In some embodiments, the composition delivers of one or more active ingredients dermally (cutaneously). In some embodiments, the composition delivers one or more active ingredients transdermally (subcutaneously). It will be appreciated by a person skilled in the art having regard to the present disclosure that adapting the compositions for dermal vs transdermal delivery of an active ingredient involves adapting the concentration or presence of certain components of the composition. For example, compositions for transdermal delivery would typically include the penetration enhancer (e.g. ethoxy diglycol) and would have higher concentrations of the liquid oil.

In an embodiment, the composition comprising one or more active ingredients has at least 3 months shelf life, at least 6 months shelf life and/or up to 2 years shelf file.

In an embodiment, the composition releases the one or more active ingredients for a time of up to about 24 hours. In another embodiment, the composition releases the one or more active ingredients for a time of about 6 hours to about 24 hours or about 12 hours to about 24 hours.

Some compositions of the present disclosure are suitable to be used as a base for preparing a compound comprising one or more active ingredients (e.g. pharmaceutical, cosmeceutical, dermaceutical, nutraceutical, phytoceutical and/or cannabinoid active ingredients). Accordingly, in some embodiments, the composition is devoid of active ingredients (is a compounding base). In an embodiment, such a composition has up to 2 years shelf life.

The present disclosure further includes a use of such compositions for preparing a compound comprising one or more active ingredients.

In alternative embodiments, the composition further comprises one or more active ingredients. In an embodiment, the one or more active ingredients are selected from pharmaceutical active ingredients, cosmeceutical active ingredients, dermaceutical active ingredients, nutraceutical active ingredients, phytoceutical active ingredients, cannabinoid active ingredients and combinations thereof. In an embodiment, the one or more active ingredients are present in a total amount of from about 5 wt % to about 40 wt %, based on the total weight of the composition. In another embodiment, the one or more active ingredients are present in a total amount of up to 30 wt %, up to 20 wt %, or up to 10 wt % based on the total weight of the composition.

In some embodiments, the composition comprises a single active ingredient. In some embodiments, the composition comprises a combination of active ingredients. In some embodiments, the composition comprises active ingredients that address different diseases, conditions or symptoms.

In some embodiments, the active ingredient or combination thereof is lipophilic. In some embodiments, the active ingredient or combination thereof is hydrophilic. In some embodiments, the active ingredients are a combination of lipophilic and hydrophilic active ingredients.

In an embodiment, the active ingredient is a pharmaceutical active ingredient. In an embodiment, the pharmaceutical active ingredient is selected from a non-steroidal anti-inflammatory drug (NSAID), a muscle relaxant, a narcotic analgesic, an opioid antagonist with analgesic effect, an opioid or opiate agonist, a nerve depressant, an antidepressant, a local anesthetic, a peripheral vasodilator, a corticosteroid, vitamin $D_3$, an anti-infective drug (e.g. an antimicrobial, antifungal and/or antiviral drug) and combinations thereof. In an embodiment, the pharmaceutical active ingredient is an NSAID. In another embodiment, the pharmaceutical active ingredient is a muscle relaxant. In another embodiment, the pharmaceutical active ingredient is a narcotic analgesic. In another embodiment, the pharmaceutical active ingredient is an opioid antagonist with analgesic effect. In another embodiment, the pharmaceutical active ingredient is an opioid or opiate agonist. In another embodiment, the pharmaceutical active ingredient is a nerve depressant. In another embodiment, the pharmaceutical active ingredient is an antidepressant. In another embodiment, the pharmaceutical active ingredient is a local anesthetic. In another embodiment, the pharmaceutical active ingredient is a peripheral vasodilator. In another embodiment, the pharmaceutical active ingredient is a corticosteroid. In another embodiment, the pharmaceutical active ingredient is vitamin $D_3$. In another embodiment, the pharmaceutical active ingredient is an anti-infective drug (e.g. an antimicrobial, antifungal and/or antiviral drug). In another embodiment of the present disclosure, the pharmaceutical active ingredient is a combination of two or more of an NSAID, a muscle relaxant, a narcotic analgesic, an opioid antagonist with analgesic effect, an opioid or opiate agonist, a nerve depressant, an antidepressant, a local anesthetic, a peripheral vasodilator, a corticosteroid, vitamin $D_3$ and an anti-infective drug (e.g. an antimicrobial, antifungal and/or antiviral drug).

In an embodiment, the NSAID is selected from a salicylic acid derivative (e.g. aspirin, diflunisal, salsalate or trilisate); a propionic acid (e.g. flurbiprofen, ibuprofen, ketoprofen, naproxen or oxaprozin); an acetic acid (e.g. diclofenac, etodolac, indomethacin, ketorolac, nabumetone, sulindac or tolmetin); a fenamate (e.g. meclofenamate); an oxicam (e.g. meloxicam or piroxicam); and a COX-2 inhibitor (e.g. celecoxib, rofecoxib, and valdecoxib). In an embodiment, the composition comprises an NSAID or combination thereof in an amount of from about 1 wt % to about 30 wt %, based on the total weight of the composition. In an embodiment, the muscle relaxant is cyclobenzaprine or baclofen. In an embodiment, the narcotic analgesic is ketamine or tramadol. In an embodiment, the opioid antagonist with analgesic effect is naltrexone. In an embodiment, the opioid or opiate agonist is ketamine or tramadol. In an embodiment, the nerve depressant is gabapentin, pregabalin, topiramate or lamotrigine. In an embodiment, the antidepressant is amitrptyline, doxepine, buproprione or naltrexone. For example, such antidepressants can optionally be used as topical analgesic drugs. In an embodiment, the local anesthetic is lidocaine (e.g. lidocaine base or lidocaine HCl), benzocaine, prilocaine HCl or tetracaine HCl. In an embodiment, the peripheral vasodilator is sildenafil, tadalafil or vardenafil. In an embodiment, the corticosteroid is hydrocortisone, betamethasone, clobetasol, desonide, fluoroquinolone or mometasone. In an embodiment, the anti-infective drug (e.g. the antimicrobial, antifungal and/or antiviral drug) is fusidic acid, mupirocin, gentamycin, neomycin or acyclovir.

In an embodiment, the active ingredient is a hormone for delivery to the dermis, e.g. for the management of skin aging. In another embodiment, the hormone is for hormone-replacement therapy. In an embodiment, the hormone is estradiol, estriol, progesterone, dehydroepiandrosterone (DHEA) or combinations thereof. In another embodiment, the hormone is testosterone.

In an embodiment, the active ingredient is a lipophilic phytoceutical. In another embodiment, the lipophilic phytoceutical is selected from a cannabinoid, methyl salicylates, curcumin, terpenoids, flavonoids and combinations thereof. In an embodiment, the cannabinoid is selected from cannabidiol, tetrahydrocannabinol, cannabinol, cannabigerol and combinations thereof. In another embodiment of the present disclosure, the terpenoids and flavonoids are selected from cineol, linanool, limonene, eucalyptol, menthol and combinations thereof.

In an embodiment, the active ingredient is a cosmeceutical. In an embodiment, the cosmeceutical is selected from a lipophilic antioxidant, ceramides and combinations thereof. In an embodiment, the cosmeceutical is a lipophilic antioxidant or combinations thereof. In another embodiment, the cosmeceutical is ceramides. In another embodiment, the lipophilic antioxidant is selected from vitamin E derivatives (e.g. alpha-tocopherol), vitamin A derivatives (e.g. retinol, beta-carotene or retinoic acid), and Coenzyme $Q_{10}$ (e.g. ubiquinol or ubiquinone).

In another embodiment, the active ingredient is a matrix metalloproteinase enhancer (e.g. stratifin), a co-enzyme for matrix metalloproteinase (e.g. zinc), a matrix metalloproteinase inhibitor, an anti-aging active (e.g. vitamin C (ascorbic acid) or glutathione), an anti-aging amino acid, peptide, protein or derivative thereof (e.g. acetyl octapeptide-1, the active peptide of botulinum toxin, hyaluronic acid, denatured collagen or arginine), natural moisturizing factors, telomerase activators or combinations thereof.

The compositions of the present disclosure can entrap lipophilic active ingredients such as diclofenac sodium in both the internal and external oil phase. This particular aspect can result in an immediate release of diclofenac sodium from the external phase for immediate local pain relief, followed by sustained release of the drug from the internal oil phase. The Nano-Emulsion SR Cream was thermodynamically stable for at least 6 months when diclofenac sodium was added at a 10% concentration and was even surprisingly stable with 20% diclofenac sodium.

Accordingly, in an embodiment, the active ingredient is diclofenac or a pharmaceutically acceptable salt thereof in an amount of up to 30 wt %. In an embodiment, the active ingredient is diclofenac or a pharmaceutically acceptable salt thereof in an amount of greater than about 2.3 wt %, for example, from 2.5 wt % to 30 wt %, about 5 wt % to about 15 wt % or about 5 wt % to about 10 wt %. In an embodiment, the diclofenac salt is diclofenac sodium.

The Nano-Emulsion SR Cream was also compounded with Benzocaine 20 wt %, Lidocaine 6 wt % and Tetracaine HCl 4 wt % to obtain a smooth and homogeneous product. The product was stable at room temperature in contrast to conventional creams and gels that are not resilient to such a high concentration of anesthetics and separate easily.

Accordingly, in an embodiment, the active ingredient is lidocaine, benzocaine, tetracaine, prilocaine or pharmaceutically acceptable salts thereof or combinations thereof, wherein the lidocaine, benzocaine, tetracaine, prilocaine or pharmaceutically acceptable salts thereof are each present in an amount of up to about 20 wt %, with the total concentration of the lidocaine, benzocaine, tetracaine, prilocaine or pharmaceutically acceptable salts thereof being no more than 30 wt %. In another embodiment, the active ingredient is lidocaine, benzocaine, tetracaine or pharmaceutically acceptable salts thereof or combinations thereof, wherein the lidocaine, benzocaine, tetracaine or pharmaceutically acceptable salts thereof are each present in an amount of up to about 20 wt %, with the total concentration of the lidocaine, benzocaine, tetracaine or pharmaceutically acceptable salts thereof being no more than 30 wt %. In an embodiment, the active ingredients are a combination of lidocaine, benzocaine and tetracaine or pharmaceutically acceptable salts thereof. In another embodiment, the active ingredients are benzocaine in an amount of about 20 wt %, lidocaine in an amount of about 6 wt % and tetracaine HCl in an amount of about 4 wt %.

The compositions of the present disclosure can be used for the dermal and/or transdermal delivery of cannabinoids (poorly water soluble, e.g. log P 6-7, MW: 280-315 Daltons). The Nano-Emulsion SR cream was compounded with THC distillate and CBD oil to obtain a smooth and homogeneous product. Packaged in an opaque airless pump and stored at room temperature away from excessive heat and light, no color change was observed over 12 months. Similar results were observed with a cream compounded with CBD isolate.

Accordingly, in an embodiment, the active ingredient is tetrahydrocannabinol (THC), cannabidiol (CBD) or combinations thereof. In an embodiment, the active ingredient is THC. In another embodiment, the active ingredient is CBD. In a further embodiment, the active ingredients are a combination of THC and CBD. In an embodiment, the composition comprises CBD isolate in an amount of up to about 20 wt %. In another embodiment, the composition comprises CBD oil in an amount of up to about 15 wt %. In a further embodiment, the composition comprises THC distillate in an amount of up to 20 wt %. In an embodiment, the THC is present in an amount of less than 1 gram per package of the composition.

In some embodiments, the composition further comprises one or more natural and/or herbal active agents with anti-inflammatory, analgesic or anesthetic effect. In some embodiments, the one or more natural and/or herbal active agents with anti-inflammatory, analgesic or anesthetic effect are oils (such as essential oils) and/or terpenoids or combinations thereof. In some embodiments, the one or more natural and/or herbal active agents with anti-inflammatory effect are an oil (e.g. avocado, olive or moringa oil), an essential oil (e.g., thyme, turmeric or rosemary essential oils) or combinations thereof. In some embodiments, the one or more natural and/or herbal agents with analgesic effect are an oil (e.g. wintergreen or peppermint oil), an essential oil (e.g. eucalyptus, lavender, thyme or rosemary essential oils) or combinations thereof. In some embodiments, the natural and/or herbal active agents with anesthetic effect are clove essential oil, menthol, or camphor or combinations thereof. In some embodiments, the composition further comprises one or more terpenoids with analgesic, anti-inflammatory, anesthetic, antioxidant, anti-infective (e.g. antimicrobial and/or anti-viral), anti-fibrogenic and/or anti-aging effects. In an embodiment, the terpenoids are cineol, eucalyptol, limonene, linanool, menthol or combinations thereof. The Nano-Emulsion SR cream was also compatible and stable in the presence of oils such as avocado, olive, moringa and wintergreen, essential oils such as clove, lavender, rosemary, eucalyptus, thyme, turmeric, peppermint and spearmint and terpenoids such as cineol, eucalyptol, limonene, linanool and menthol. Accordingly, in some embodiments of the present disclosure, the composition further comprises one or more oils similar to such oils and/or essential oils. In another embodiment, the essential oil is lavender, rosemary, eucalyptus, thyme, turmeric, peppermint and spearmint or combinations thereof. In another embodiment, the oil is avocado, olive, moringa or wintergreen oil or combinations thereof.

It will be appreciated by a person skilled in the art that the components of the compositions of the present disclosure can be chosen from natural, organic, cosmetic and/or pharmaceutical grade categories and can select appropriate components accordingly.

III. Methods of Delivering Active Ingredients

The compositions of the present disclosure can be used, for example, for cutaneous (dermal) and/or subcutaneous (transdermal) delivery of active ingredients, whether compounded or in a commercially available product. An exemplary compound with diclofenac sodium added at a 10% concentration showed sustained release of the diclofenac sodium for 24 hours.

Accordingly, the present disclosure also includes a method of delivering one or more active ingredients to a subject, the method comprising applying a composition of the present disclosure comprising the one or more active ingredients to the skin of the subject. The present disclosure also includes a use of a composition of the present disclosure comprising the one or more active ingredients on the skin of a subject for delivering the one or more active ingredients to the subject. The present disclosure also includes a use of a composition of the present disclosure comprising the one or more active ingredients for preparation of a medicament for the skin of a subject for delivering the one or more active ingredients to the subject. The present disclosure also includes a composition of the present disclosure comprising the one or more active ingredients for use on the skin of a subject to deliver the one or more active ingredients to the subject.

In an embodiment, the delivery of the one or more active ingredients is dermal. In another embodiment, the delivery of the one or more active ingredients is subdermal.

In an embodiment, the composition is a commercially available product. In another embodiment, the composition is prepared as a compound.

In an embodiment, the composition or compound is administered to the skin of the subject or for use less than three times per day. In another embodiment, the composition or compound is administered to the skin of the subject or for use twice per day. In a further embodiment, the composition or compound is administered to the skin of the subject or for use once per day.

It will be appreciated by a person skilled in the art that the use of the composition will depend on the active ingredient or combination of active ingredients to be delivered to the subject. For example, in some embodiments, the delivery of the one or more active ingredients is for treatment (e.g. targeted local relief) of inflammation, pain (e.g. musculoskeletal and/or neuropathic pain), muscle spasm, skin aging, tissue fibrosis, joint fibrosis or combinations thereof and the skilled person would be able to select suitable active agents accordingly. In an embodiment, the delivery of the one or more active ingredients is for local analgesic effect. In another embodiment, the delivery of the one or more active ingredients is for local-inflammatory effect. In a further embodiment, the delivery of the one or more active ingredients is for an antifibrogenic effect. In another embodiment, the delivery of the one or more active ingredients is for anti-aging and/or skin rejuvenation.

IV. Methods of Preparation

The Nano-Emulsion SR Cream described in the examples of the present disclosure was prepared using a low energy emulsification technique via hot stirring and homogenization. Such a technique can be an easy, cost-effective method to scale up. However, the choice of emulsion components and ratios of these components, as well as certain steps to add ingredients is critical in generating stable emulsion systems with appropriate particle sizes.

Accordingly, the present disclosure includes a method of preparing a composition comprising an oil-in-water nano-emulsion dispersed in an external oil phase, the oil-in-water nano-emulsion comprising an internal oil phase dispersed in an aqueous phase, the method comprising:
  combining a first mixture comprising a liquid oil and a charged lipid with a second mixture that is an aqueous mixture comprising a film-forming thermoreversible emulsifier to prepare an oil-in-water nano-emulsion; and
  combining the oil-in-water nano-emulsion with a third mixture comprising a combination of solid lipids to prepare the composition,
  wherein the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

It will be appreciated by a person skilled in the art that embodiments relating to the components of the compositions of the present disclosure may pertain to embodiments relating to the corresponding components in the methods herein for preparing such compositions.

For example, in an embodiment, the aqueous mixture comprising the film-forming thermoreversible emulsifier further comprises a humectant. The humectant can be any suitable humectant. In an embodiment, the humectant is glycerin, 1,2-propanediol, 1,3-propanediol or combinations thereof. In another embodiment, the humectant is glycerin. The compositions prepared by the methods of the present disclosure preferably have a low concentration of humectant which advantageously may, for example, reduce transepidermal water loss (TEWL). Accordingly, in a further embodiment of the present disclosure, the composition comprises less than about 2 wt % of the humectant (such as the glycerin).

The liquid oil is any suitable liquid oil or combination thereof. In an embodiment, the liquid oil is a synthetic oil, mineral oil, natural oil, essential oil or combinations thereof. In another embodiment, the liquid oil is a synthetic oil, mineral oil, natural oil or combinations thereof. In a further embodiment, the liquid oil is a mineral oil, natural oil or combinations thereof. In an embodiment, the liquid oil is a natural oil. In an embodiment, the natural oil is a vegetable oil or combination thereof. In another embodiment, the vegetable oil or combination thereof is selected from long chain triglycerides (i.e. triglycerides having an aliphatic tail of 13-21 carbon atoms), medium chain triglycerides (i.e. triglycerides having 2 or 3 fatty acids having an aliphatic tail of 6-12 carbon atoms), sources thereof or combinations thereof. A person skilled in the art would be able to readily select a suitable source or combination thereof for a particular composition of triglycerides. In an embodiment, the vegetable oil or combination thereof is selected from olive oil, medium chain triglyceride oil, coconut oil, palm oil, moringa oil, avocado oil and combinations thereof. In another embodiment, the liquid oil such as the vegetable oil or combination thereof is medium-chain triglyceride (MCT) oil. In a further embodiment, the MCT oil comprises caprylic acid (C8:0) and capric acid (C10:0) e.g. in a ratio of about 60:40. The internal oil phase is in the range of from about 1 wt % to about 20 wt %, based on the total weight of the internal oil phase, aqueous phase and external oil phase.

In an embodiment, the charged lipid is a negatively charged lipid. In an embodiment, the negatively charged lipid is a negatively charged fatty acid. The negatively charged fatty acid can be any suitable negatively charged fatty acid. Negatively charged lipids e.g. fatty acids such as oleic acid may also, for example, advantageously cause less skin irritation than positively charged lipids. Accordingly, in an embodiment, the negatively charged lipid is oleic acid. In another embodiment, the charged lipid is a positively charged lipid. In another embodiment, the positively charged lipid is a positively charged fatty amine. In another embodiment of the present disclosure, the positively charged fatty amine is oleyl amine.

In an embodiment, the ratio by weight of the liquid oil to the charged lipid is in a range of from about 5:1 to about 10:1.

In an embodiment, the film-forming thermoreversible emulsifier is an amphoteric tri-block copolymer. In another embodiment, the film-forming thermoreversible emulsifier is a polyethylene glycol-b-polypropylene glycol-b-polyethylene glycol. In another embodiment, the polyethylene glycol-b-polypropylene glycol-b-polyethylene glycol is Poloxamer 407 (Pluronic™ F-127), Poloxamer 188 (Pluronic™ F-68) or combinations thereof. In an embodiment, the polyethylene glycol-b-polypropylene glycol-b-polyethylene glycol is Poloxamer 407. The film-forming thermoreversible emulsifier is present in an amount suitable to stabilize the nano-emulsion. In an embodiment, the ratio by weight of the film-forming thermoreversible emulsifier to the internal oil phase is at least 0.1:10, e.g. at least 0.3:10.

In an embodiment, the combination of solid lipids is a combination of at least two of
(i) glyceryl dibehenate, glyceryl palmitostearate or combinations thereof;
(ii) petrolatum, cetyl palmitate, beeswax or combinations thereof;
(iii) a hydrogenated vegetable oil or combinations thereof;
(iv) a fatty alcohol or combinations thereof; and
(v) glyceryl stearate, polyethylene glycol (PEG)-40 glyceryl stearate, PEG-100 stearate or combinations thereof.

In an embodiment, the glyceryl dibehenate, glyceryl palmitostearate or combinations thereof is glyceryl dibehenate. In another embodiment, the petrolatum, cetyl palmitate, beeswax or combinations thereof is petrolatum. In another embodiment, the petrolatum is petrolatum white USP. In another embodiment, the petrolatum, cetyl palmitate, beeswax or combinations thereof is beeswax. In an embodiment, the hydrogenated vegetable oil is hydrogenated castor oil, hydrogenated soy oil or combinations thereof. In another embodiment, the hydrogenated vegetable oil is hydrogenated castor oil. In an embodiment, the fatty alcohol or combination thereof is cetyl alcohol, stearyl alcohol, cetostearyl alcohol (a mixture of fatty alcohols comprising predominantly cetyl alcohol and stearyl alcohol) or combinations thereof. In another embodiment, the fatty alcohol is cetyl alcohol. In another embodiment, the glyceryl stearate, polyethylene glycol (PEG)-40 glyceryl stearate, PEG-100 stearate or combinations thereof is a combination of glyceryl stearate and PEG-100 stearate. In an embodiment, the ratio of the solid lipids (i):[(ii)+(iii)]:(v) in the combination is about 2:1:2. In another embodiment, the solid lipids comprise, consist essentially of or consist of glyceryl dibehenate, petrolatum (e.g. petrolatum white USP), hydrogenated castor oil, cetyl alcohol, glyceryl stearate and PEG-100 stearate.

In an embodiment, the third mixture comprising the combination of solid lipids further comprises a liquid emollient, a penetration enhancer, an antioxidant, or combinations thereof. In another embodiment, the third mixture comprising the combination of solid lipids further comprises a liquid emollient, a penetration enhancer and an antioxidant.

The liquid emollient can be polar or non-polar and suitably has the ability to dissolve soluble and poorly water-soluble active ingredients, respectively. The liquid emollient is advantageously of amino acid or vegetable origin or is a silicone oil and has the advantage of a lack of a rancid oil odor. Accordingly, in an embodiment, the liquid emollient is isopropyl myristate, isopropyl palmitate, glycine, N-methyl-N-(1-oxododecyl)-, 1-methylethyl ester (isopropyl lauroyl sarcosinate) a plant-based C15-19 Alkane (e.g. EMOGREEN™) or a silicone oil emollient. Such emollients may, for example, have enhanced ceramide-like emolliency (sensory effect), reduced greasy feeling and/or reduced oxidative reactions (thereby avoiding or reducing the development of a rancid oil smell. In an embodiment of the present disclosure, the liquid emollient is isopropyl lauroyl sarcosinate.

Penetration enhancers suitably create a push and pull effect. As a result, they can enhance the skin reservoir effect and sustain the release of poorly soluble active ingredients. While dimethyl sulfoxide (DMSO) is a commonly used solvent for enhancing the penetration of lipophilic drugs, ethoxy diglycol is advantageous in that it has less skin toxicity. Accordingly, in an embodiment, the penetration enhancer is ethoxy diglycol. The Nano-Emulsion SR cream was also compatible and stable in the presence of terpenoids useful e.g. as natural penetration enhancers such as cineol, eucalyptol limonene, linanool and menthol. Accordingly, in some embodiments of the present disclosure, the penetration enhancer comprises a natural penetration enhancer. In another embodiment, the natural penetration enhancer is one or more terpenoids or combinations thereof. In another embodiment, the terpenoid is cineol, eucalyptol limonene, linanool, menthol or combinations thereof. In another embodiment, the penetration enhancer comprises menthol.

Antioxidants can be useful, for example, to prevent or reduce oxidation of oil ingredients and/or discoloration of active ingredients such as cannabinoids. The antioxidants are suitably selected from natural or synthetic antioxidants. In an embodiment, the antioxidant is tocopherol acetate, butylated hydroxytoluene (BHT), butylated hydroxyanisole (BHA) or combinations thereof. In another embodiment, the antioxidant is butylated hydroxytoluene.

In an embodiment, the third mixture comprising the combination of solid lipids comprises: the liquid emollient isopropyl lauroyl sarcosinate; the penetration enhancer ethoxy diglycol; and the antioxidant butylated hydroxytoluene.

In an embodiment, subsequent to preparing the oil-in-water nano-emulsion, the method further comprises:
combining the oil-in-water nano-emulsion with a fourth mixture comprising one or more of a multifunctional polymer and a chelating agent.

Accordingly, the present disclosure also includes a method of preparing a composition comprising an oil-in-water nano-emulsion dispersed in an external oil phase, the oil-in-water nano-emulsion comprising an internal oil phase dispersed in an aqueous phase, the method comprising:
combining a first mixture comprising a liquid oil and a charged lipid with a second mixture that is an aqueous mixture comprising a film-forming thermoreversible emulsifier to prepare an oil-in-water nano-emulsion;
combining the oil-in-water nano-emulsion with a fourth mixture comprising one or more of a multifunctional polymer and a chelating agent; and
combining the oil-in-water nano-emulsion thereby obtained with a third mixture comprising a combination of solid lipids to prepare the composition,
wherein the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

In such embodiments, the multifunctional polymer is well-hydrated by combining with the first mixture prior to combination with the third mixture so as to obtain a homogeneous composition. In an embodiment, the multifunctional polymer comprises one or more tri-block copolymers having a hydrophilic-lipophilic balance (HLB) of about 18. In another embodiment, the multifunctional polymer is combination of polyacrylamide & C13-14 isoparaffin & laureth-7 (e.g. SEPIGEL™ 305), acrylamide/sodium acryloyldimethyl taurate copolymer, isohexadecane and Polysorbate 80 (e.g. SIMULGEL™ 600), a hydroxyethyl acrylate/sodium acryloyldimethyl taurate copolymer (e.g. SEPINOV™ WEO and/or SEPINOV EMT-10), polyacrylate crosspolymer-6 (e.g. SEPIMAX ZEN™) polyacrylate crosspolymer-11 (e.g. ARISTOFLEX™ Velvet) or combinations thereof. The multifunctional polymers are suitably selected from those that are stable in a wide pH range. For example, polyacrylate crosspolymer-6, has advantageous resistance to electrolytes and is stable in a wide pH range (from about 2 to about 8). It has the ability to stabilize the oil phase, provide a gel cream texture and create a pseudo-emulsion system. In an embodiment, the multifunctional polymer is a combination of multifunctional polymers that is polyacrylate crosspolymer-6 and hydroxyethyl acrylate/sodium acryloyldimethyl taurate copolymer.

The chelating agent is any suitable chelating agent. In an embodiment, the chelating agent is a salt (e.g. a disodium salt) of ethylenediaminetetraacetic acid (EDTA).

In an embodiment, the multifunctional polymer is a combination of multifunctional polymers that is polyacrylate crosspolymer-6 and hydroxyethyl acrylate/sodium acryloyldimethyl taurate copolymer and the chelating agent is disodium ethylenediaminetetraacetic acid (EDTA).

In an embodiment, subsequent to combining the oil-in-water nano-emulsion with the third mixture comprising a combination of solid lipids, the method further comprises combining the composition thereby obtained with a preservative.

Accordingly, the present disclosure also includes a method of preparing a composition comprising an oil-in-water nano-emulsion dispersed in an external oil phase, the oil-in-water nano-emulsion comprising an internal oil phase dispersed in an aqueous phase, the method comprising:
combining a first mixture comprising a liquid oil and a charged lipid with a second mixture that is an aqueous mixture comprising a film-forming thermoreversible emulsifier to prepare an oil-in-water nano-emulsion;
combining the oil-in-water nano-emulsion thereby obtained with a fourth mixture comprising one or more of a multifunctional polymer and a chelating agent;
combining the oil-in-water nano-emulsion with a third mixture comprising a combination of solid lipids; and
combining the composition thereby obtained with a preservative to prepare the composition,
wherein the ratio by weight of the oil-in-water nano-emulsion to the external oil phase is in a range of from about 2:3 to about 7:3; and the ratio by weight of the liquid oil to the charged lipid is in a range of from about 5:1 to about 50:1.

The preservative is suitably a wide spectrum preservative or combination thereof capable of preserving both oil and water phases. The preservative is suitably selected from natural and/or synthetic preservatives. In an embodiment, the preservative is caprylyl glycol, pentylene glycol, ethylhexylglycerin, Vitamin E, phenoxy ethanol or combinations thereof. In another embodiment of the present disclosure, the preservative is a combination of preservatives that is caprylyl glycol and phenoxy ethanol.

In an embodiment, the composition comprises, consists essentially of or consists of
water e.g. in an amount of from about 50 wt % to about 80 wt %;
glycerin e.g. in an amount of from about 1 wt % to about 10 wt %;
polyethylene glycol-b-polypropylene glycol-b-polyethylene glycol e.g. in an amount of from about 0.05 wt % to about 5 wt %;
oleic acid e.g. in an amount of from about 0.1 wt % to about 10 wt %;
MCT oil e.g. in an amount of from about 1 wt % to about 10 wt %;
polyacrylate crosspolymer-6 e.g. in an amount of from about 0.1 wt % to about 5 wt %;
hydroxyethyl acrylate/sodium acryloyldimethyl taurate copolymer e.g. in an amount of from about 0.1 wt % to about 5 wt %;
disodium EDTA e.g. in an amount of from about 0.005 wt % to about 0.05 wt %;
glyceryl dibehenate e.g. in an amount of from about 1 wt % to about 10 wt %;
petrolatum (e.g. petrolatum white USP) e.g. in an amount of from about 0.5 wt % to about 10 wt %;
hydrogenated castor oil e.g. in an amount of from about 1 wt % to about 10 wt %; cetyl alcohol e.g. in an amount of from about 0.5 wt % to about 10 wt %;
glyceryl stearate and PEG-100 stearate e.g. in an amount of from about 1 wt % to about 10 wt %;
isopropyl lauroyl sarcosinate e.g. in an amount of from about 1 wt % to about 5 wt %;
ethoxy diglycol e.g. in an amount of from about 1 wt % to about 10 wt %;

butylated hydroxytoluene e.g. in an amount of from about 0.02 wt % to 0.1 wt %;

caprylyl glycol e.g. in an amount of from about 0.01 wt % to about 1.0 wt %; and phenoxy ethanol e.g. in an amount of from about 0.05 wt % to about 1.0 wt %.

The speed at which the combining (e.g. mixing) in the present methods is carried out may, for example, have an impact on the particle size in the compositions prepared therefrom. For example, a higher rate of mixing may result in a smaller particle size in the nano-emulsions. In the examples of the present disclosure, a high shear homogenizer was used. However, other suitable means for combining in the methods of the present disclosure can also be employed such as an ultra-sonicator or a high-pressure homogenizer. For example, a high-pressure homogenizer may be useful to obtain nano-emulsions having an average droplet size of less than about 500 nm whereas a high shear homogenizer may be useful to obtain nano-emulsions having an average droplet size of greater than about 500 nm. Accordingly, in an embodiment, the combining comprises mixing with a high shear homogenizer, an ultra-sonicator or a high-pressure homogenizer. In another embodiment, the combining comprises mixing with a high shear homogenizer. The temperature at which the combining (e.g. mixing) in the present methods is carried out may, for example, be selected based on the temperature sensitivity of the components (e.g. any active ingredients being added during the method). In an embodiment, the combining is carried out at a temperature of from about 35° C. to about 85° C. In another embodiment, the combining comprises mixing with a high shear homogenizer at a temperature of from about 35° C. to about 85° C. The time period for combining may depend, for example, on the components being combined and the step of the method but can be selected by a person skilled in the art having regard to the present disclosure. In an embodiment, the time for combining the first mixture with the second mixture is from about 15 minutes to about 1 hour or about 30 minutes. In another embodiment, the time for combining the oil-in-water nano-emulsion with the fourth mixture is from about 15 minutes to about 1 hour or about 30 minutes. In a further embodiment, the time for combining the oil-in-water nano-emulsion with the third mixture is from about 5 minutes to about 30 minutes or about 15 minutes. In another embodiment, the time for combining the composition obtained from combining the oil-in-water nano-emulsion with the third mixture is from about 5 minutes to about 20 minutes or about 10 minutes.

The order of combining may vary. For example, the first mixture may be added to the second mixture or vice versa. However, adding the third mixture comprising the combination of solid lipids to the oil-in-water nano-emulsion may be advantageous during manufacturing due to the respective volumes of these components. Accordingly, in an embodiment, the combination of solid lipids is added to the oil-in-water nano-emulsion.

In some embodiments, the method does not comprise adding an active ingredient. In an embodiment, the method is for preparation of a compounding base.

In alternative embodiments, the method further comprises adding one or more active ingredients, natural and/or herbal active agents with anti-inflammatory, analgesic, anesthetic, anti-aging, anti-fibrogenic and/or anti-infective effect; terpenoids; essential oils or combinations thereof. The embodiments for the active ingredients, natural and/or herbal active agents with anti-inflammatory, analgesic, anesthetic, anti-aging, anti-fibrogenic and/or anti-infective effect; terpenoids; essential oils or combinations thereof can be varied as described herein above.

In some embodiments, the addition is by a method comprising compounding (i.e. the composition is in the form of a compound base). A person skilled in the art would be able to readily select means and suitable conditions for compounding. In such embodiments, additional excipients such as a levigating agent (e.g. ethoxy diglycol) are mixed with powdered active ingredients or other components to be added prior to addition to the composition.

In alternative embodiments, the addition is during the preparation of the composition; i.e. the one or more active ingredients, natural and/or herbal active agents with anti-inflammatory, analgesic, anesthetic, anti-aging, anti-fibrogenic and/or anti-infective effect; terpenoids; essential oils or combinations thereof are combined with the other components of the composition to obtain the composition. The step at which the addition is carried out as well as the conditions (e.g. temperature) may vary depending on the particular active ingredients and/or their physicochemical stability, natural and/or herbal active agents with anti-inflammatory, analgesic, anesthetic, anti-aging, anti-fibrogenic and/or anti-infective effect; terpenoids; essential oils or combinations thereof which are being added but can be readily selected by a person skilled in the art.

The present disclosure also includes a composition obtained by a method of the present disclosure for preparing a composition comprising an oil-in-water nano-emulsion dispersed in an external oil phase, the oil-in-water nano-emulsion comprising an internal oil phase dispersed in an aqueous phase.

The following non-limiting examples are illustrative of the present disclosure:

EXAMPLES

Example 1: Preparation and Characterization of a Nano-Emulsion Cream Useful for Transdermal Delivery and Studies of its Use for Sustained Release of Diclofenac Sodium I. Materials Phase A: Purified water (62%); glycerin (humectant; 2%); and Poloxamer 407 (thickening, stabilizing emulsifier; 0.3%). Phase B: Oleic acid (lipid component with negative charge; 1%); and medium chain triglyceride (non-hydrogenated oil, penetration enhancer and emollient; 8%). Phase C: polyacrylate crosspolymer-6 (oil and water thickening, stabilizing emulsifier; 0.6%); hydroxyethyl acrylate/sodium acryloyldimethyl taurate copolymer (oil and water thickening, stabilizing co-emulsifier; 0.2%); and disodium ethylenediaminetetraacetic acid (EDTA, chelating agent; 0.02%). Phase D: cetyl alcohol (fatty alcohol thickener; 2%); glyceryl stearate and PEG-100 stearate (emulsifying thickener; 5.5%), white petrolatum USP (semi-occlusive lipid component; 1%); hydrogenated castor oil (solid lipid component; 1.75%); glyceryl dibehenate (solid lipid with sustained release property; 5.5%); isopropyl lauroyl sarcosinate (amino acid based polar emollient; 3%); butylated hydroxy toluene (anti-oxidant; 0.1%); and ethoxy diglycol (permeation enhancer, solubilizing agent; 5%). Phase E: caprylyl glycol preservative; 0.5%); and phenoxyethanol (preservative; 0.9%).

II. General Preparation of Nano-Emulsion SR Cream

Phase A: Purified water was heated to 60° C. then glycerin added, while heating continued at 60° C. Poloxamer 407 was then added as a 30% stock solution in water while mixing with a high shear homogenizer and heating to 80° C. the temperature was maintained at 80° C.

Phase B: In another vessel, all of the components of Phase B were mixed and the temperature brought to 80° C. by heating. The temperature was maintained at 80° C.

While maintaining the temperature at 80° C., the Phase B mixture was then added into the Phase A vessel while mixing with a high shear homogenizer at 8000 rpm while maintaining the temperature at 80° C. The mixture was homogenized using the high shear homogenizer for 30 minutes and the temperature continued to be maintained at 80° C.

Phase C: The Phase C components were then added into the Phase A/B (nano-emulsion) while mixing with the high shear homogenizer while maintaining the temperature at 80° C. and mixed for 30 minutes at 8000-rpm. The temperature was maintained at 80° C.

Phase D: In another vessel, all of the components of Phase D were mixed, and the temperature brought to 80° C. by heating. The temperature was maintained at 80° C.

At 80° C., the Phase D mixture was then added into the Phase A/B/C mixture while mixing with the high shear homogenizer at high speed while maintaining the temperature at 80° C. The mixture was mixed with the high shear homogenizer for 15 minutes.

The batch was then cooled to 50° C. and the temperature maintained at 50° C.

Phase E: The Phase E premix was then prepared in a separate container and the mixture warmed enough to melt the caprylyl glycol.

At 50° C., the Phase E premix was added into the batch containing the remaining phases while mixing with the high shear homogenizer. The mixture was mixed for 10 minutes then cooled to room temperature where the initial pH was recorded (pH range: 4.5-5.5).

III. Thermodynamic Stability (Product Shelf Life)

An accelerated stability test was conducted for the Nano-Emulsion SR Cream over a period of three months as per ICH guidelines at a temperature of 40±2° C./and 75% relative humidity (RH). Triplicate samples were analyzed for changes in the appearance (odor, color and any sign of phase separation), pH and viscosity. The product was stable for 3 months under accelerated conditions, which corresponds to 2 years shelf life for the Nano-Emulsion SR cream.

IV. Nano-Emulsion Droplet Size Measurement

A nano-emulsion composed of oleic acid (1 ml), MCT oil (8 ml), Poloxamer 407 (30% stock Solution, 1 ml), glycerin (2 ml) and water (63 ml) was prepared. The aqueous and oil phases were heated separately to 80° C. The oil phase was gradually added to aqueous phase, mixed and homogenized at 8000 rpm using a high shear homogenizer for 30 minutes while temperature was maintained at 80° C. Samples were cooled down, diluted 10,000-15,000 times using distilled water and mixed well. The Z value (droplet size) was measured at 25° C. using a Malvern Zetasizer Nano-ZS. Measurements were conducted using 6 preparations (n=6). Mean values were calculated. The mean droplet size measured 498 nm.

Example 2: Compounding with Diclofenac Sodium

I. Preparation

Diclofenac sodium (micronized, 10 g) powder was ground using a mortar and pestle. Levigating agent (ethoxy diglycol, 3 mL) was added to wet the powder and form a smooth paste. The Nano-emulsion SR cream of Example 1 was geometrically added and the components mixed well until homogenous. For example, an overhead stirrer or a compounding mixer can be used to mix the compound. The compound was packaged in an airless pump container and can be suitably stored at room temperature away from excessive heat.

II. In Vitro Permeation Test Through PermeaPad™ Membrane

Three replicates of 10% diclofenac sodium compounded cream was tested on a PermeaPad biomimetic membrane. In-line diffusion cells with a diameter of 11.28 mm (1 cm$^2$) were used for the testing. An InnoMe GmbH PermeaPad Membrane was used as a synthetic skin membrane. Cells were dosed by filling a syringe with the 10% diclofenac sodium cream, and then using the syringe to apply the material (15 mg to 40 mg) directly to each of the membranes, taking weights of the syringe before and after. Phosphate buffer (pH 7.4) was used as the receptor fluid. Flow rate was set to 1 mL/hr. Samples were collected at 1, 3, 6, 9, 12, 16, 20, and 24 hours. Samples were refrigerated at 3° C. for 6 days before high performance liquid chromatography HPLC analysis was performed. The HPLC method was isocratic with 72% methanol and 28% of a mixture of pH 2.85 phosphoric acid and 0.5% triethylamine on an Agilent Zorbax eclipse XDB-C18 column (5 μm 4.6 mm×150 mm) maintained at 40° C. Retention time for diclofenac was determined to be 6.3 minutes. No interference compounds were present.

Figure 2:
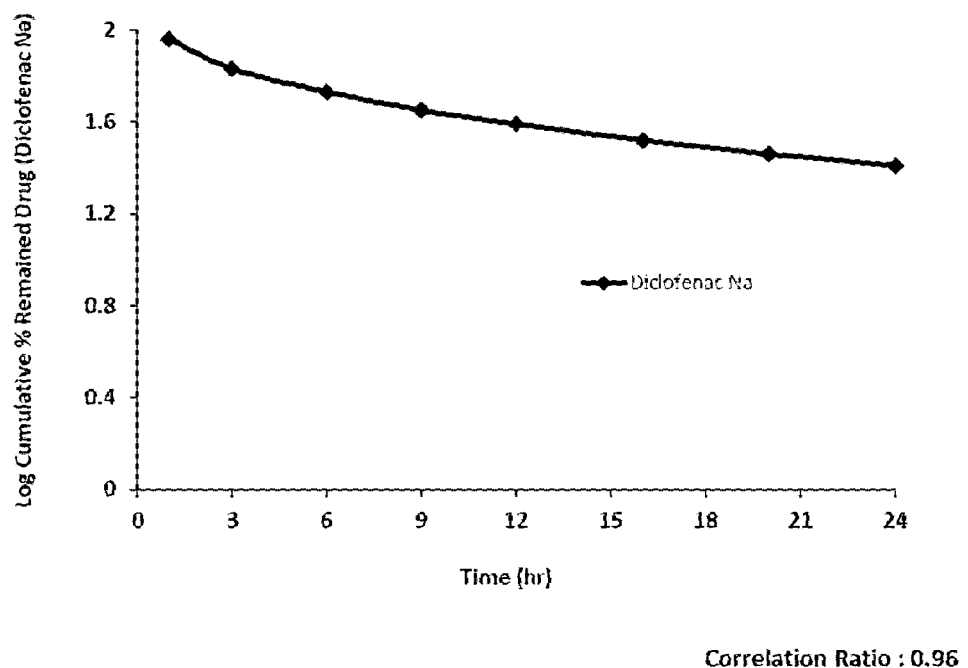
FIG. 2 is a plot showing in vitro permeation test first order release kinetics of the diclofenac sodium (Diclofenac Na) from the nano-emulsion SR composition according to an embodiment of the present disclosure tested by in vitro permeation through PermeaPad™ membranes.
Figure 3:
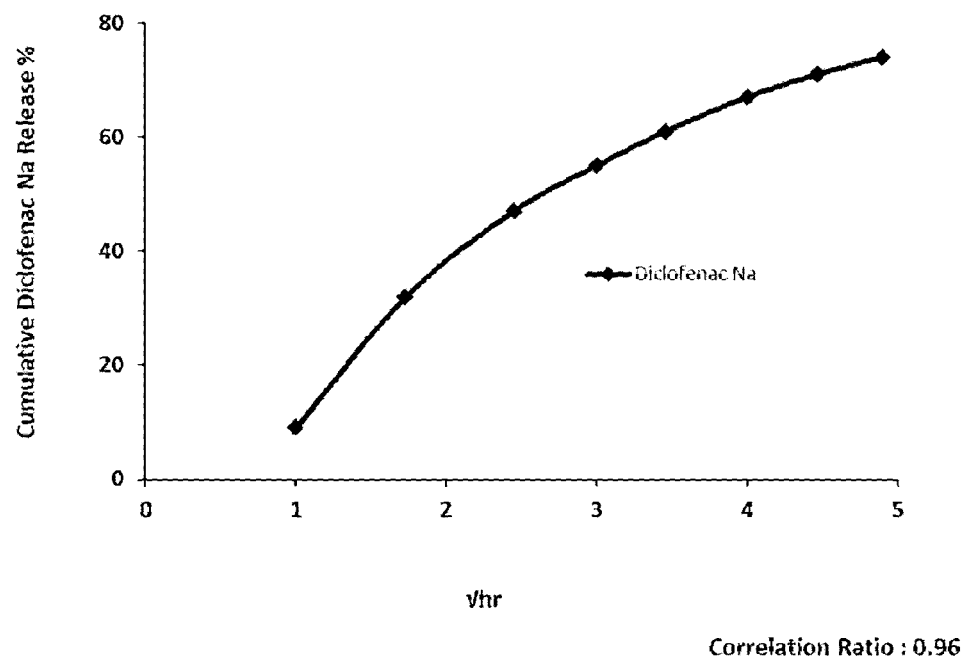
FIG. 3 is a plot showing in vitro permeation test Higutchi release kinetics of the diclofenac sodium (Diclofenac Na) from the nano-emulsion SR composition according to an embodiment of the present disclosure tested by in vitro permeation through PermeaPad™ membranes.
Figure 4:
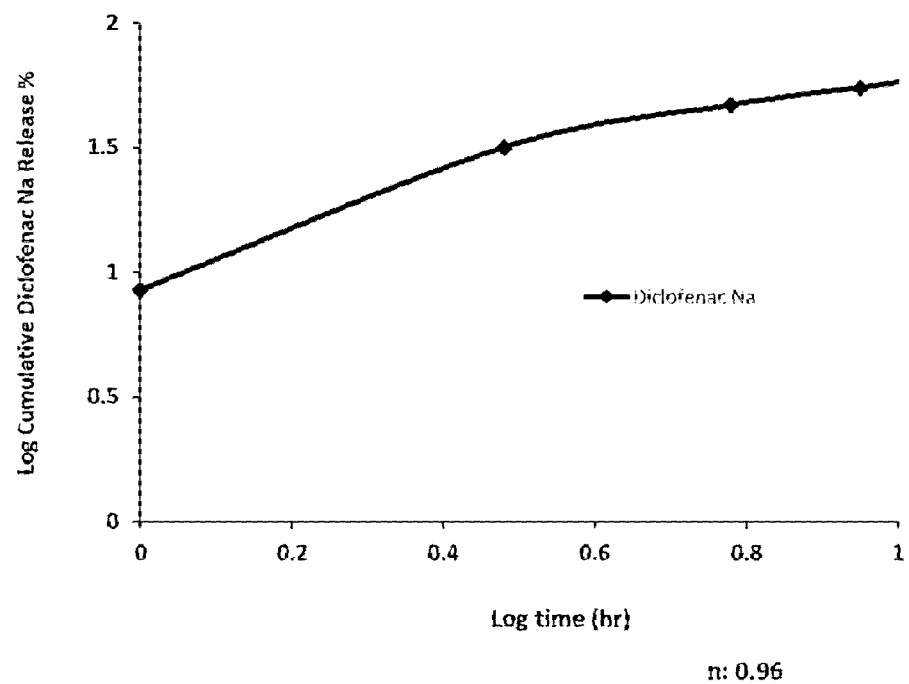
FIG. 4 is a Korsmeyer-Peppas model plot of the release kinetics of the diclofenac sodium (Diclofenac Na) from the nano-emulsion SR composition according to an embodiment of the present disclosure tested by in vitro permeation through PermeaPad™ membranes.

The results indicated a sustained release pattern throughout 24 hours of the study (FIG. 1). Drug (diclofenac sodium) release kinetics indicated that drug release was best explained by first-order kinetics, as these plots showed the highest linearity (Correlation Coefficient=0.9696; FIG. 2), but a close relationship was also noted with Higutchi kinetics (Correlation Coefficient=0.9694; FIG. 3). Korsmeyer Peppas's plot indicated an "n" value of 0.9729 (FIG. 4), which was indicative of an anomalous diffusion mechanism or diffusion coupled with matrix dissolution; hence, the drug release was controlled by more than one process. Drug dissolution and as a result drug release from this formulation is impacted by the presence of penetration enhancers, such as MCT oil, ethoxy diglycol and oleic acid. Additionally, while not wishing to be limited by theory, the film-forming and semi occlusive property of the nano-emulsion SR cream impacts on the degradation of the matrix created by hydrogenated castor oil, glyceryl behenate, cetyl alcohol, petrolatum and glyceryl monostearate by creating water channels and therefore matrix porosity. The in vitro permeation results show that the rate of drug release is concentration dependent (first-order kinetics). The higher rate of release was observed for the initial 60% of drug released (16 hours) was followed by a slightly slower rate between 16 to 24 hours. The concentration dependent rate of release would be a useful tool, for example, for pharmacists and physicians in customizing the compounding formulation strength (% of active drug) to a patient's needs.

III. Thermodynamic Stability (Beyond Use Date)

Accelerated (40±2° C. and 75% RH) and real time (25° C. and 60% RH) stability tests were conducted for the Nano-Emulsion SR cream compounded with diclofenac Na 10%. Triplicate preparations were also analyzed for changes in the appearance (odor, color and signs of phase separation), pH, viscosity, microbial contamination (yeast and mold, *Staphylococcus aureus, Escherichia coli, Salmonella,* and *Pseudomonas*) and drug content (potency; evaluated using the HPLC method) of the compound. Samples were tested at time zero, and after 7, 21 and 42 days. The real time samples were tested after 90 and 180 days. The results of the accelerated stability test were confirmed by a real time stability test.

The results showed that the Nano-Emulsion SR cream compounded with diclofenac Na was stable for 180 days. There was no significant change in the appearance of the compound, pH and viscosity of the product. The active drug content reduced by 3.7% following 42 days kept in the accelerated condition, which is well under the accepted limit for compounded product potency variation limit (±10%). Furthermore, real time stability results confirmed the stability of the diclofenac Na 10% compounded in the Nano-Emulsion SR cream up to at least 180 days. Therefore, a BUD of 180 days was assigned to this preparation.

Decreasing the dose frequency of drugs such as nonsteroidal anti-inflammatory drugs (NSAIDs) like diclofenac Na may, for example, increase patient compliance; patients prefer to apply the cream once daily. It can also reduce the cost of a drug for patient significantly. The O/W/O Nano-Emulsion cream sustained the release of diclofenac Na for 24 hours. Hence, the formulation can, for example, be used as a once-daily sustained-release transdermal cream for targeted local pain and inflammation relief. The formulation showed exceptional thermodynamic stability, 6 months, when compounded with diclofenac Na 10%. Additionally, the full plate microbial count showed no contamination at the end of stability test.

IV. Additional Observations

The diclofenac Na 10% compounded in Nano-Emulsion SR was dispensed to individual patients with knee arthritis, shoulder neuropathic pain and back pain. The patients reported 30 minutes onset of action followed by 18-20 hours sustained pain relief. Pain was controlled well overnight and there was no breakthrough pain to wake up patients. The semi-occlusive property of the cream was noticeable and acknowledged by patients.

Example 3: Compounded Anesthetic Cream (BLT Cream)

Topical Benzocaine 20%, Lidocaine 6% and Tetracaine HCl 4% (BLT) is commonly prescribed for local anesthesia prior to dermatological procedures. However, the conventional creams and gels are not resilient to such a high concentration of anesthetics and separate easily. The Nano-Emulsion SR Cream of Example 1 was used for compounding this prescription.

| | |
|---|---|
| Benzocaine | 20 g |
| Lidocaine | 6 g |
| Tetracaine HCl | 4 g |
| Ethoxy Diglycol | 10 ml |
| Nano-Emulsion SR Cream (Example 1) | qs to 100 g |

Lidocaine crystalline powder was triturated using a mortar and pestle. Tetracaine and then benzocaine powders were geometrically added to the lidocaine fine powder. The powders were ground and blended well. Ethoxy diglycol was then added to the powders and mixed to form a smooth paste. The Nano-Emulsion SR Cream was geometrically added and mixed using an overhead stirrer or a compounding mixer (electronic mortar and pestle). The BLT cream was packaged in an airless pump and can be kept at room temperature or refrigerated.

The compounded product was smooth and homogeneous. It was stable at room temperature. According to USP guidelines for topical compounded products, a BUD of 35 days was assigned to this compound (United States Pharmacopeia, General Chapter 795, Pharmaceutical Compounding—Non-Sterile Preparations, USP 42-NF 37, 2019). The BLT cream was dispensed to patients. The patients reported 18-20 hours local anesthesia.

Example 4: Compounded Product Containing Multiple Analgesic Drugs

This compound contained one NSAID (diclofenac Na), one nerve depressant (gabapentin), and one anesthetic (lidocaine). This compound may be used for neuropathic pain, sciatic pain, trigeminal neuralgia and pain associated with shingles.

| | |
|---|---|
| Diclofenac Na | 10 g |
| Gabapentin | 6 g |
| Lidocaine | 5 g |
| Ethoxy Diglycol | 4 ml |
| Nano-Emulsion SR Cream (Example 1) | qs to 100 g |

Gabapentin and Lidocaine crystalline powders were triturated and blended well using a mortar and pestle. Diclofenac Na powder was then added and blended well. Ethoxy diglycol was added to levigate the powders and to form a smooth paste. The Nano-Emulsion SR Cream was geometrically added to the powders and mixed well until a smooth and homogeneous mixture was achieved. The compounded cream was packaged in an opaque airless pump. The product was stored in room temperature away from excessive heat.

A BUD of 90 days can be assigned to this preparation when stored at room temperature (25° C.) due to low stability profile of gabapentin and lidocaine. The cream was dispensed to 5 patients. The patients reported 18-20 hours local anesthesia.

Example 5: Compounded Product Containing Multiple Drugs

This compounded preparation contains more than one drug. In particular, it includes two NSAIDs (diclofenac Na and ketoprofen), one muscle relaxant (baclofen), and one antidepressant (amitriptyline). This compound is indicated for musculoskeletal pain.

| | |
|---|---|
| Diclofenac Na | 10 g |
| Ketoprofen | 10 g |
| Baclofen | 5 g |
| Amitriptyline HCl | 2 g |
| Ethoxy Diglycol | 6 ml |
| Nano Emulsion SR Cream (Example 1) | qs to 100 g |

Amitriptyline HCl, baclofen, diclofenac Na and ketoprofen powders were ground and then geometrically blended using a mortar and pestle. Ethoxy diglycol was added to levigate the powders and to form a smooth paste. The Nano-Emulsion SR cream was geometrically added to the powders and mixed well until a smooth and homogeneous mixture was achieved. The compounded cream was packaged in an opaque airless pump. The product was stored in room temperature away from excessive heat. The BUD of this preparation is 180 days at room temperature (25° C.).

Example 6: Compounded Product Containing Multiple Analgesic Drugs

This compounded preparation contains more than one analgesic drug. It includes one NSAID (diclofenac Na) and one muscle relaxant (cyclobenzaprine HCl). This compound may be used for musculoskeletal pain.

| Diclofenac Na | 10 g |
|---|---|
| Cyclobenzaprine HCl | 2 g |
| Ethoxy Diglycol | 3 ml |
| Nano Emulsion SR Cream (Example 1) | qs to 100 g |

Cyclobenzaprine HCl and diclofenac Na powders were ground and geometrically mixed using a mortar and pestle. Ethoxy diglycol was added to levigate the powders and to form a smooth paste. The Nano-Emulsion SR cream was geometrically added to the powders and mixed well until a smooth and homogeneous mixture was achieved. The compounded cream was packaged in an opaque airless pump. The product was stored in room temperature away from excessive heat. The BUD of this preparation is 90 days at room temperature (25° C.) due to the low stability profile of cyclobenzaprine HCl.

Example 7: Compounded Product with High Concentration of an NSAID

This compounded preparation contains a higher concentration of the NSAID diclofenac Na than the preparations of the Examples hereinabove.

| Diclofenac Na | 20 g |
|---|---|
| Ethoxy Diglycol | 5 ml |
| Nano-Emulsion SR Cream (Example 1) | qs to 100 g |

Diclofenac Na micronized powder was ground using a mortar and pestle. Ethoxy diglycol was then added to levigate the powder and to form a smooth paste. The Nano-Emulsion SR cream was geometrically added to the powders and mixed well until a smooth and homogeneous mixture was achieved. The compounded cream was packaged in an opaque airless pump. The product was stored at room temperature away from excessive heat. The BUD of this preparation is 180 days at room temperature (25° C.).

Example 8: Formulation Containing CBD/THC

Full spectrum Oil (3:33% (w/v) THC:CBD in MCT Oil) 9 ml (270 mg: 891 mg THC:CBD)

| THC Distillate (99%) | 230 mg |
|---|---|
| Menthol | 0.5 g |
| Nano-Emulsion SR cream (Example 1) | qs to 50 g |

Menthol crystals were ground using a mortar and pestle until they became liquid. In a glass beaker, the THC distillate and CBD oil were gently heated up to 40° C. while mixing with a glass stirrer. This mixture was added to the menthol and mixed well. The Nano-Emulsion SR cream was then geometrically added to the mixture and mixed well until a smooth and homogeneous mixture achieved. The compounded cream was packaged in an opaque airless pump. The product was stored at room temperature away from excessive heat and light.

The mixture was smooth and homogenous. The mixture was kept at room temperature for 12 months (tested every week for the first month and then monthly up to 12 months). The mixture was consistent and homogenous. No color change was observed for the 12 months tested.

Example 9: Formulation Containing CBD Isolate

| CBD Isolate (99%) | 500 mg |
|---|---|
| Menthol | 0.5 g |
| Spearmint Essential Oil | 0.5 ml |
| Nano-Emulsion SR Cream (Example 1) | qs to 50 g |

Menthol crystals were ground using a mortar and pestle until they became liquid. Then spearmint and CBD oil were added and mixed well. The Nano-Emulsion SR cream was then geometrically added to the mixture and mixed well until a smooth and homogeneous mixture achieved. The compounded cream was packaged in an opaque airless pump. The product was stored at room temperature away from excessive heat and light.

The mixture was smooth and homogenous. The mixture was kept at room temperature for 12 months (tested every week for the first month and then monthly up to 12 months). The mixture was consistent and homogenous. No color change was observed for the 12 months tested.

Comparative Example

Phase A: Purified water (80 wt %), glycerin (1 wt %) and Poloxamer 407 (0.3 wt %). Phase B: Oleic acid (1 wt %), MCT (8 wt %), cetyl alcohol (2 wt %), glyceryl stearate and PEG-100 stearate (5 wt %), and isononyl isononanoate (2 wt %). Phase C: Polyacrylate Crosspolymer-6 (0.7 wt %).

In this experiment, the oil phase (Phase B) and aqueous phase (Phase A) were heated to 80° C. separately. Phase B was added to Phase A while homogenizing at 8000 rpm. The droplet size of the cream was measured with a Zetasizer. The result showed that the droplet size was in the micrometer range (1.5 to 3 μm). This formulation did not create a nano-emulsion.

While the disclosure has been described with reference to what are presently considered to be the preferred examples, it is to be understood that the disclosure is not limited to the disclosed examples. To the contrary, the present disclosure is intended to cover various modifications and equivalent arrangements included within the spirit and scope of the appended claims.

What is claimed is:

1. A composition comprising an oil-in-water nano-emulsion dispersed in an external oil phase, the oil-in-water nano-emulsion comprising an internal oil phase dispersed in an aqueous phase and stabilized by a film-forming thermoreversible emulsifier, wherein the film-forming thermoreversible emulsifier is an amphoteric tri-block copolymer, wherein the internal oil phase comprises a liquid oil in combination with a charged lipid;
the aqueous phase comprises water in an amount of from about 50 wt % to about 80 wt %, based on the total weight of the internal oil phase, aqueous phase and external oil phase;
the external oil phase comprises a combination of solid lipids;
the ratio by weight of the oil-in-water nano-emulsion to the external oil phase is in a range of from about 2:3 to about 8.5:3; the ratio by weight of the liquid oil to the charged lipid is in a range of from about 5:1 to about 50:1; and the composition further comprises a multifunctional polymer or combinations thereof as a thickener and stabilizer of the oil-in-water nano-emulsion.

2. The composition of claim 1, wherein the aqueous phase further comprises a humectant.

3. The composition of claim 2, wherein the humectant is glycerin; wherein the liquid oil is medium chain triglyceride (MCT) oil; wherein the charged lipid is a negatively charged lipid; and wherein the amphoteric tri-block copolymer is a polyethylene glycol-block-polypropylene glycol-block-polyethylene glycol.

4. The composition of claim 1, wherein the ratio by weight of the film-forming thermoreversible emulsifier to the internal oil phase is at least 0.1:10.

5. The composition of claim 1, wherein the combination of solid lipids is a combination of at least two of:
   (i) glyceryl dibehenate, glyceryl palmitostearate or combinations thereof;
   (ii) petrolatum, cetyl palmitate, beeswax or combinations thereof;
   (iii) a hydrogenated vegetable oil or combinations thereof;
   (iv) a fatty alcohol or combinations thereof; and
   (v) glyceryl stearate, polyethylene glycol (PEG)-40 glyceryl stearate, PEG-100 stearate or combinations thereof.

6. The composition of claim 5, wherein the ratio by weight of (i):[(ii)+(iii)]:(v) in the combination of solid lipids is about 2:1:2.

7. The composition of claim 2, wherein:
   the combination of multifunctional polymers is polyacrylate crosspolymer-6 and hydroxyethyl acrylate/sodium acryloyldimethyl taurate copolymer;
   the external oil phase further comprises:
     the liquid emollient isopropyl lauroyl sarcosinate;
     the penetration enhancer ethoxy diglycol; and
     the antioxidant butylated hydroxytoluene;
   the aqueous phase further comprises:
     the chelating agent disodium ethylenediaminetetraacetic acid (EDTA); and
     a combination of preservatives that is caprylyl glycol and phenoxy ethanol.

8. The composition of claim 7, wherein:
   the humectant is glycerin;
   the amphoteric tri-block copolymer is polyethylene glycol-block-polypropylene glycol-blockpolyethylene glycol;
   the negatively charged lipid is oleic acid;
   the liquid oil is medium chain triglyceride (MCT) oil; and
   the combination of solid lipids are glyceryl dibehenate, petrolatum, hydrogenated castor oil, cetyl alcohol, glyceryl stearate and PEG-100 stearate, and
   the composition comprises:
     the glycerin in an amount of from about 1 wt % to about 10 wt %;
     the polyethylene glycol-block-polypropylene glycol-block-polyethylene glycol in an amount of from about 0.05 wt % to about 5 wt %;
     the oleic acid in an amount of from about 0.1 wt % to about 10 wt %;
     the medium chain triglyceride (MCT) oil in an amount of from about 1 wt % to about 10 wt %;
     the polyacrylate crosspolymer-6 in an amount of from about 0.1 wt % to about 5 wt %;
     the hydroxyethyl acrylate/sodium acryloyldimethyl taurate copolymer in an amount of from about 0.1 wt % to about 5 wt %;
     the disodium EDTA in an amount of from about 0.005 wt % to about 0.05 wt %;
     the glyceryl dibehenate in an amount of from about 1 wt % to about 10 wt %;
     the petrolatum in an amount of from about 0.5 wt % to about 10 wt %;
     the hydrogenated castor oil in an amount of from about 1 wt % to about 10 wt %;
     the cetyl alcohol in an amount of from about 0.5 wt % to about 10 wt %;
     the glyceryl stearate and PEG-100 stearate in an amount of from about 1 wt % to about 10 wt %;
     the isopropyl lauroyl sarcosinate in an amount of from about 1 wt % to about 5 wt %;
     the ethoxy diglycol in an amount of from about 1 wt % to about 10 wt %;
     the butylated hydroxytoluene in an amount of from about 0.02 wt % to 0.1 wt %;
     the caprylyl glycol in an amount of from about 0.01 wt % to about 1.0 wt %; and
     the phenoxy ethanol in an amount of from about 0.05 wt % to about 1 wt %.

9. The composition of claim 8, wherein the composition is a compounding base or a drug delivery base.

10. A composition comprising the composition of claim 1, and further comprising one or more active ingredients selected from pharmaceutical active ingredients, cosmeceutical active ingredients, dermaceutical active ingredients, nutraceutical active ingredients, phytoceutical active ingredients, cannabinoid active ingredients and combinations thereof.

11. The composition of claim 10, wherein the active ingredient is diclofenac or a pharmaceutically acceptable salt thereof.

12. The composition of claim 11, wherein the diclofenac or pharmaceutically acceptable salt thereof is diclofenac sodium present in an amount of from about 5 wt % to about 10 wt %.

13. The composition of claim 10, wherein the active ingredients are lidocaine, benzocaine, tetracaine or pharmaceutically acceptable salts thereof or combinations thereof, wherein the lidocaine, benzocaine, tetracaine or pharmaceutically acceptable salts thereof are present in an amount of up to about 20 wt %, with the total concentration of the lidocaine, benzocaine, tetracaine or pharmaceutically acceptable salts thereof being no more than 30 wt %, based on the total weight of the composition.

14. The composition of claim 10, wherein the active ingredient is tetrahydrocannabinol (THC), cannabidiol (CBD) or combinations thereof.

15. A method of delivering one or more active ingredients to a subject, the method comprising applying a composition of claim 10 to the skin of the subject.

16. A method of preparing the composition of claim 1, the method comprising:
   combining a first mixture comprising the liquid oil and the charged lipid with a second mixture that is an aqueous mixture comprising the film-forming thermoreversible emulsifier to prepare an oil-in-water nano-emulsion;
   combining the oil-in-water nano-emulsion thereby obtained with a fourth mixture comprising the multifunctional polymer or combinations thereof; and
   combining the oil-in-water nano-emulsion with a third mixture comprising the combination of solid lipids to prepare the composition.

17. The method of claim 16, wherein the fourth mixture further comprises a chelating agent.

18. The method of claim 17, wherein subsequent to combining the oil-in-water nano-emulsion with the third mixture comprising the combination of solid lipids, the method further comprises combining the composition thereby obtained with a preservative.

19. The method of claim 18, wherein:
the second mixture further comprises the humectant glycerin;
the amphoteric tri-block copolymer is polyethylene glycol-block-polypropylene glycol-block-polyethylene glycol;
the negatively charged lipid is oleic acid;
the liquid oil is medium chain triglyceride (MCT) oil;
the combination of multifunctional polymers is polyacrylate crosspolymer-6 and hydroxyethyl acrylate/sodium acryloyldimethyl taurate copolymer;
the chelating agent is disodium ethylenediaminetetraacetic acid (EDTA); the combination of solid lipids are glyceryl dibehenate, petrolatum, hydrogenated castor oil, cetyl alcohol, glyceryl stearate and PEG-100 stearate;
the third mixture comprising the combination of solid lipids further comprises: the liquid emollient isopropyl lauroyl sarcosinate; the penetration enhancer ethoxy diglycol; and the antioxidant butylated hydroxytoluene; and
the preservative is a combination of preservatives that is caprylyl glycol and phenoxy ethanol, and
the composition comprises:
the glycerin in an amount of from about 1 wt % to about 10 wt %;
the polyethylene glycol-block-polypropylene glycol-block-polyethylene glycol in an amount of from about 0.05 wt % to about 5 wt %;
the oleic acid in an amount of from about 0.1 wt % to about 10 wt %;
the medium chain triglyceride (MCT) oil in an amount of from about 1 wt % to about 10 wt %;
the polyacrylate crosspolymer-6 in an amount of from about 0.1 wt % to about 5 wt %;
the hydroxyethyl acrylate/sodium acryloyldimethyl taurate copolymer in an amount of from about 0.1 wt % to about 5 wt %;
the disodium EDTA in an amount of from about 0.005 wt % to about 0.05 wt %;
the glyceryl dibehenate in an amount of from about 1 wt % to about 10 wt %;
the petrolatum in an amount of from about 0.5 wt % to about 10 wt %;
the hydrogenated castor oil in an amount of from about 1 wt % to about 10 wt %;
the cetyl alcohol in an amount of from about 0.5 wt % to about 10 wt %;
the glyceryl stearate and PEG-100 stearate in an amount of from about 1 wt % to about 10 wt %;
the isopropyl lauroyl sarcosinate in an amount of from about 1 wt % to about 5 wt %;
the ethoxy diglycol in an amount of from about 1 wt % to about 10 wt %;
the butylated hydroxytoluene in an amount of from about 0.02 wt % to 0.1 wt %;
the caprylyl glycol in an amount of from about 0.01 wt % to about 1.0 wt %; and
the phenoxy ethanol in an amount of from about 0.05 wt % to about 1 wt %.

20. The method of claim 19, wherein the method further comprises adding one or more active ingredients selected from pharmaceutical active ingredients, cosmeceutical active ingredients, dermaceutical active ingredients, nutraceutical active ingredients, phytoceutical active ingredients, cannabinoid active ingredients and combinations thereof.

21. The composition of claim 8, wherein the ratio by weight of the oil-in-water nano-emulsion to the external oil phase is about 8.5:3.

22. The method of claim 19, wherein the ratio by weight of the oil-in-water nano-emulsion to the external oil phase is about 8.5:3.

23. The composition of claim 8, wherein the ratio by weight of the oil-in-water nano-emulsion to the external oil phase is about 8.5:3; the ratio by weight of the liquid oil to the charged lipid is about 8:1,
and the composition comprises:
the water in an amount of about 62 wt %;
the glycerin in an amount of about 2 wt %;
the polyethylene glycol-block-polypropylene glycol-block-polyethylene glycol in an amount of about 0.3 wt %;
the oleic acid in an amount of about 1 wt %;
the medium chain triglyceride (MCT) oil in an amount of about 8 wt %;
the polyacrylate crosspolymer-6 in an amount of about 0.6 wt %;
the hydroxyethyl acrylate/sodium acryloyldimethyl taurate copolymer in an amount of about 0.2 wt %;
the disodium ethylenediaminetetraacetic acid in an amount of about 0.02 wt %;
the glyceryl dibehenate in an amount of about 5.5 wt %;
the petrolatum in an amount of about 1 wt %;
the hydrogenated castor oil in an amount of about 1.75 wt %;
the cetyl alcohol in an amount of about 2 wt %;
the glyceryl stearate and PEG-100 stearate in an amount of about 5.5 wt %;
the isopropyl lauroyl sarcosinate in an amount of about 3 wt %;
the ethoxy diglycol in an amount of about 5 wt %;
the butylated hydroxytoluene in an amount of 0.1 wt % or less than 0.1 wt %;
the caprylyl glycol in an amount of about 0.5 wt %; and
the phenoxy ethanol in an amount of about 0.9 wt %.

\* \* \* \* \*